United States Patent [19]

Kumar et al.

[11] Patent Number: 5,399,497
[45] Date of Patent: * Mar. 21, 1995

[54] CAPSULE CHEMISTRY SAMPLE LIQUID ANALYSIS SYSTEM AND METHOD

[75] Inventors: Anand Kumar, Monroe; Paul Gherson, Yorktown Heights; Milt Pelavin, Somers, all of N.Y.

[73] Assignee: Miles, Inc., Tarrytown, N.Y.

[*] Notice: The portion of the term of this patent subsequent to Dec. 7, 2010 has been disclaimed.

[21] Appl. No.: 106,254

[22] Filed: Aug. 13, 1993

Related U.S. Application Data

[63] Continuation-in-part of Ser. No. 846,269, Feb. 26, 1992, Pat. No. 5,268,147.

[51] Int. Cl.$^6$ .............................................. G01N 35/08
[52] U.S. Cl. ........................................... 436/53; 436/52; 422/68.1; 422/81; 422/82; 73/863.21; 73/863.71
[58] Field of Search ................ 422/68.1, 73, 81, 82, 422/100, 101; 436/52, 53; 73/863.21, 863.71; 210/222, 634, 645, 695

[56] References Cited

U.S. PATENT DOCUMENTS

| | | | |
|---|---|---|---|
| 3,970,518 | 7/1976 | Giaever | 195/1.5 |
| 4,018,886 | 4/1977 | Giaever | 424/12 |
| 4,141,687 | 2/1979 | Forrest et al. | 23/230 R |
| 4,219,335 | 8/1980 | Ebersole | 23/230 B |
| 4,253,846 | 3/1981 | Smythe et al. | 23/230 R |
| 4,259,291 | 3/1981 | Smythe | 422/82 |
| 4,297,337 | 10/1981 | Mansfield et al. | 424/1 |
| 4,298,478 | 11/1981 | Watson et al. | 210/695 |
| 4,398,894 | 8/1983 | Yamamoto | 436/517 |
| 4,418,039 | 11/1983 | Adler | 422/82 |
| 4,444,659 | 4/1984 | Beeltz et al. | 210/222 |
| 4,452,773 | 6/1984 | Molday | 424/1.1 |
| 4,517,302 | 5/1985 | Saros | 436/180 |
| 4,562,157 | 12/1985 | Lowe et al. | 435/291 |
| 4,595,494 | 6/1986 | Kukuck | 209/224 |
| 4,628,037 | 12/1986 | Chagnon et al. | 436/526 |
| 4,657,868 | 4/1987 | Saxholm | 435/287 |
| 4,677,067 | 6/1987 | Schwartz et al. | 435/177 |
| 4,728,500 | 3/1988 | Higo | 422/99 |
| 4,731,337 | 3/1988 | Luotola et al. | 436/526 |
| 4,738,773 | 4/1988 | Müller-Ruchholtz et al. | 209/214 |
| 4,745,077 | 5/1988 | Holian et al. | 436/526 |
| 4,777,145 | 10/1988 | Luotola et al. | 436/526 |
| 4,784,758 | 11/1988 | Willis | 209/214 |
| 4,853,336 | 8/1989 | Saros et al. | 436/53 |
| 4,855,045 | 8/1989 | Reed | 210/223 |
| 4,910,148 | 3/1990 | Sorensen et al. | 435/317.1 |
| 4,913,883 | 4/1990 | Imai et al. | 422/82.01 |
| 4,916,081 | 4/1990 | Kamada et al. | 436/526 |
| 5,045,473 | 9/1991 | Cassaday et al. | 436/53 |
| 5,123,901 | 6/1992 | Carew | 604/5 |
| 5,130,027 | 6/1992 | Noble et al. | 210/656 |
| 5,134,079 | 7/1992 | Cusack et al. | 436/53 |
| 5,135,720 | 8/1992 | Uchida | 422/107 |
| 5,147,529 | 9/1992 | Lee et al. | 210/695 |
| 5,158,871 | 10/1992 | Rossomando et al. | 435/7.32 |
| 5,186,827 | 2/1993 | Liberti et al. | 210/222 |

Primary Examiner—James C. Housel
Assistant Examiner—Long V. Le
Attorney, Agent, or Firm—Sprung Horn Kramer & Woods

[57] ABSTRACT

An analysis method and apparatus comprises feeding a stream of fluid capsules in a fluid conduit for flow therethrough by forming a film of isolating liquid on an inner surface of the conduit and randomly accessing each of a plurality of liquids selected from a sample liquid, reagents and a magnetic particle suspension to form a plurality of isolated segments from the plurality of liquids in each capsule in the conduit. The fluid capsules flow in at least one longitudinal direction of the conduit and the suspended magnetic particles are selectively magnetically retained from one segment in one capsule at a given location for placement of the magnetic particles in another segment in the one capsule during the flow of the one capsule through the conduit. The fluid capsules are then measured in the conduit.

23 Claims, 30 Drawing Sheets

CAPSULE CHEMISTRY SAMPLE LIQUID ANALYSIS SYSTEM AND METHOD

This application is a continuation-in-part application of U.S. application Ser. No. 07/846,269, filed on Feb. 26, 1992 and now W. S. Pat. No. 5,268,147.

BACKGROUND OF THE INVENTION

Field of The Invention

This invention relates to a capsule chemistry sample liquid analysis system and method which, although suitable for application to a wide variety of analyses on a wide variety of sample liquids, are particularly adapted to the automated clinical analyses in turn of pluralities of human biological sample liquids.

A large number of ligand binding assays, such as immunoassays and DNA probe assays, are carried out on a solid phase. This allows separation of the target analyte species from interfering species, reduction in background signal and measurements of analytes in physiological specimens at very low concentration levels.

In automated instruments, magnetic particles are the most desirable solid phase. However, these automated instruments tend to be more complex because of the additional mechanisms required for the washing and separation of the magnetic particles.

SUMMARY OF THE INVENTION

The main object of the present invention is to provide for the washing and separation of the magnetic particles in an automated instrument.

Another object of the present invention is to provide a simple structure for an automated instrument for magnetic particle-based assays which has built-in wash cycles which require no additional mechanisms and hardware.

These and other objects of the present invention are achieved in accordance with the present invention by adapting the magnetic particle-based assays to capsule chemistry technology.

DESCRIPTION OF THE DRAWINGS

The above and other significant objects and advantages of the sample liquid analysis system and method of our invention are believed made clear by the following detailed description thereof taken in conjunction with the accompanying drawings, wherein.

DETAILED DESCRIPTION OF THE INVENTION

Figure 1:
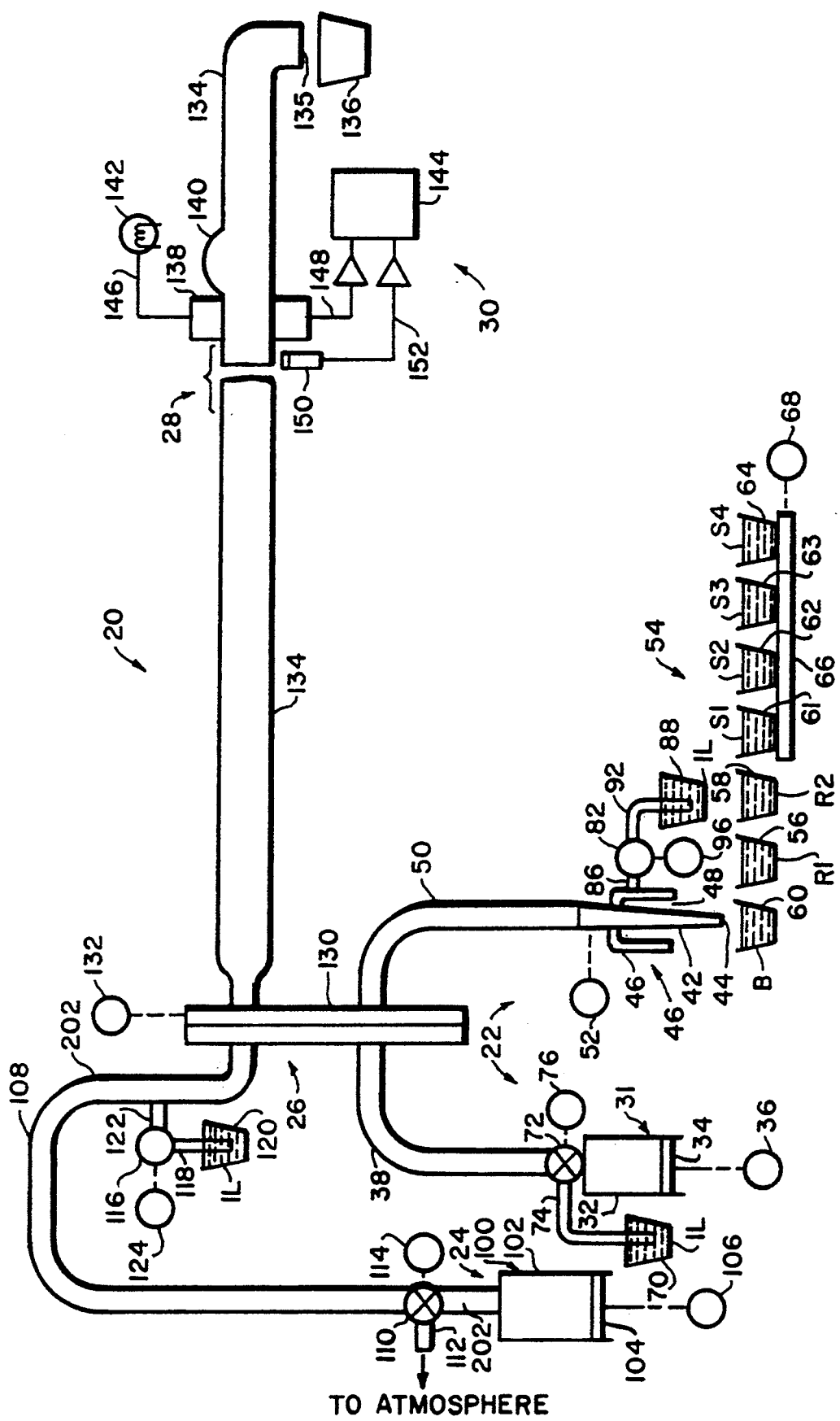
FIG. 1 is an essentially schematic diagram illustrating a first embodiment of a reversible direction sample liquid analysis system representatively configured and operable in accordance with the currently contemplated best mode of our invention.

Referring now to FIG. 1 of the application drawings, a first embodiment of the reversible direction capsule chemistry sample liquid analysis system representatively configured and operable in accordance with the currently contemplated best mode of our invention is schematically depicted as indicated generally at 20: and comprises sample liquid test package metering and supply means as indicated generally at 22 which operate to meter successive encapsulated test packages of sample, reagents and buffer liquids, and air and supply the same in turn for reaction and analysis within the system; reversible direction sample liquid test package displacement means as indicated generally at 24 which operate to bi-directionally displace the thusly metered and supplied test packages through the system; test package transfer means as generally indicated at 26 which operate in conjunction with the test package metering and supply means 22 and the test package displacement means 24 to provide for the successive test package supply and bi-directional functions of the system; test package reaction and analysis means as indicated generally at 28 for the successive reactions and repeated analyses of the thusly supplied and displaced test packages; and detection means as indicated generally at 30 which are operatively associated with the reaction and analysis means 28 to detect and quantify the successive sample liquid test packages analysis results.

The test package metering and supply means 22 comprise a precisely operable, highly accurate positive displacement pump, for example a piston pump as indicated at 31, comprising pump cylinder 32 and pump piston 34 driven as indicated by an electric drive motor as indicated at 36 and operatively connected thereto as shown. A flexible conduit of any appropriately durable, inert and transparent material, for example Teflon which is also hydrophobic, is indicated at 38 and operatively connects pump cylinder 32 as shown to what will hereinafter be termed the "upstream" side of the sample liquid test package transfer means 26 for the supply of successive test packages thereto as described in greater detail hereinbelow.

Further included in the test package metering and supply means 22 is a sample liquid test package aspirating probe assembly as indicated generally at 40, and which preferably takes the general form of that disclosed in U.S. Pat. No. 4,121,466 issued Oct. 24, 1978 to Allen Reichler, et al, and assigned to the assignee hereof; the disclosure of which is hereby incorporated by reference in this specification. As such, probe assembly 40 comprises a rigid probe tube 42, again preferably of Teflon or like material, having an inlet end 44, and an outer probe tube 46 located concentrically as shown around probe tube 42 and sealed thereto to form an annular chamber 48 therearound. A flexible conduit 50, again preferably of transparent Teflon or like material, operatively connects probe tube 42 as shown to what will hereinafter be termed the "downstream" side of sample test package transfer means 26, and therethrough to conduit 38 and pump 31, as and for purposes described in detail hereinbelow.

Probe drive means taking the form of an electric drive motor are indicated at 52, and are operatively connected as shown to probe tube 42 for drive of the probe assembly 40 in conventional manner.

Sample, reagent and buffer liquid supply means are indicated generally at 54 in FIG. 1; and, for a representative application of the system 20 of our invention, comprise a container 56 of reagent liquid R1, container 58 of reagent liquid R2, and container 60 for an appropriate buffer liquid B. An array of sample liquid containers for different, essentially aqueous sample liquids, only four of which are illustrated as indicated at 61, 62, 63 and 64 for the containers, and S1, S2, S3 and S4 for the different sample liquids contained therein, are operatively disposed in any suitable transport device as indicated at 66, for example the sample carrier block and shuttle assembly as disclosed in detail in U.S. Pat. No. 4,853,336 issued Aug. 1, 1989 to Stephen Saros et al, and assigned to the assignee hereof; the disclosure of which is hereby incorporated by reference in this specification. The transport device 66 is intermittently driven by an electric drive motor 68 operatively connected thereto as shown to index the included sample liquid containers in turn for access by probe tube 42 and sample liquid aspiration therefrom. Although not shown, it will be readily understood by those skilled in this art that liquid level sensing means of any appropriate, well known configuration are preferably operatively associated with probe assembly 40 to provide for precisely reproducible aspirations of the sample, reagent and buffer liquids from the respective containers thereof in the formation of the sample liquid test packages.

Further included in the sample liquid test package metering and supply means 22 is an isolation liquid supply reservoir as indicated at 70, and which is disposed as shown adjacent pump 30 to contain an appropriate quantity of an isolation liquid as indicated at IL. For representative use of the system 20 of our invention with essentially aqueous sample, reagent and buffer liquids, and hydrophobic system probe and conduit components, isolation liquid IL will be constituted by an appropriate fluoro-carbon or silicon liquid which is immiscible with the sample, reagent and buffer liquids, and which preferentially wets the hydrophobic inner walls of the hydrophobic system components to the substantial exclusion of those liquids, thereby coating those system component inner walls with an isolation liquid layer to substantially prevent contact therewith by said liquids and the adhesion of the same thereto. This significantly reduces sample liquid carryover, i.e. the contamination of succeeding sample liquid by the residue of a preceding sample liquid, and thus significantly increases the overall accuracy of the sample liquid analysis results. This technique of sample liquid carryover minimization through use of an immiscible isolation liquid has now become well known in the automated sample liquids analysis art as disclosed for example in U.S. Pat. No. 4,865,993 issued Sep. 12, 1989 to Michael M. Cassaday, et al and assigned to the predecessor in interest of the assignee hereof; the disclosure of which is hereby incorporated by reference in this specification.

A three way rotary valve is indicated at 72, and is operatively disposed as shown in conduit 38 immediately at the outlet from pump cylinder 32; and an isolation liquid supply conduit 74 operatively connects valve 72 to the supply of isolation liquid IL within reservoir 70. Rotary valve 72 is driven by an operatively connected electric drive motor as indicated at 76 between a first valve position wherein the valve connects pump cylinder 32 directly through conduit 38 to the upstream side of transfer means 26, and a second valve position wherein the valve connects pump cylinder 32 and conduit 38 to the isolation liquid reservoir 70 through supply conduit 74 for the suppply of the isolation liquid IL thereto as and for the purposes described in detail hereinbelow.

A precisely operable positive displacement pump, for example a syringe pump is indicated at 82 in FIG. 1, and is connected as shown by flexible conduit 86 to the annular probe chamber 48 through outer probe tube 46. An isolation liquid reservoir is indicated at 88; and conduit 92 connects pump 82 thereto as shown. Electric drive motor is indicated at 96, and is operatively connected as shown to pump 82 to drive the same, thereby pumping the isolation liquid IL from reservoir 88 into the annular space 48 between the outer and inner probe tubes 46 and 42 through conduits 92 and 86; all to result in the formation of a layer of the isolation liquid on the outer surface of probe tube 42 for effective sample liquid carryover minimization with regard to the probe assembly 40 as made clear in U.S. Pat. No. 4,121,466 referenced hereinabove. In addition, a sample liquid carryover-minimizing layer of the isolation liquid IL is also formed and maintained on the inner surface of the probe tube 42 as described in detail hereinbelow.

The reversible direction test package displacement means 24 of FIG. 1 comprise a highly accurate positive displacement piston pump 100 which includes pump cylinder 102 and pump piston 104 driven as indicated by an electric drive motor 106 operatively connected thereto as shown. A flexible conduit, again preferably of transparent Teflon or like material, is indicated at 108 and operatively connects pump cylinder 102 to the upstream side of the sample liquid test package transfer means 26 as shown. A three way rotary valve is indicated at 110, and is operatively disposed as shown in conduit 108 above pump 100. A vent conduit 112 connects valve 110 to atmosphere. Valve 110 is driven as indicated by an operatively connected drive motor 114 between a first valve position wherein the same closes vent conduit 112; and a second valve position wherein the valve connects conduit 108, and thus pump cylinder 102, to atmosphere through vent conduit 112.

Further included in the test package displacement means 24 of FIG. 1 is a precisely operable positive displacement pump, again for example a syringe pump, as indicated at 116. Pump 116 is operatively connected as shown by conduit 118 to a supply of the isolation liquid IL as contained in isolation liquid reservoir 120 disposed as shown below pump 116; and is connected as shown to conduit 108 by flexible branch conduit 122. An electric drive motor is indicated at 124 and is operatively connected to pump 116 as shown to drive the same and supply isolation liquid IL from reservoir 120 through branch conduit 122 to conduit 108, again for sample liquid carryover minimization purposes as described in detail hereinbelow.

The test package transfer means 24 of FIG. 1 comprise a two position linear shear valve as indicated at 130. Valve 130 is driven by shown by an operatively connected electric drive motor 132 between what will hereinafter be termed an "aspirate" position wherein the valve connects conduit 38, and thus pump 31, to conduit 50, and thus probe assembly 40, and simultaneously connects conduit 108, and thus pump 100, to the test package reaction and analysis means 28; and what will hereinafter be termed a "transfer" position wherein the valve 130 connects conduit 38, and thus pump 31, to the test package reaction and analysis means 28, while simply closing off conduits 50 and 108 at the valve; both as described in greater detail hereinbelow.

The test package reaction and analysis means 28 of FIG. 1 comprise an analytical line as indicated at 134, and formed by a generally elongated, flexible transparent conduit of Teflon or like material, which extends as shown from operative connection to the downstream side of shear valve 130 to terminate in an open end 135 above a waste container 136 for the flow of the duly reacted and analyzed sample liquid test packages from the line in turn into that waste container. A flow cell of essentially conventional configuration and manner of operation is indicated at 138, and is operatively disposed as shown in analytical line 134 for the bi-directional flow of the sample liquid test packages therethrough in turn as described in greater detail hereinbelow.

Further included in the analytical line 134 immediately downstream of flow cell 138 is an aneurism, or section of enlarged cross-sectional area, as indicated at 140 and which is preferably formed integrally with the line, for example by blow-molding, thereby eliminating sample liquid carryover-intensive joints in the analytical line 134 as will be well understood by those skilled in this art. In the manner disclosed in U.S. Pat. No. 4,853,336 referenced hereinabove, this section 140 of enlarged cross-sectional area, hereinafter referred to as the "vanish zone," operates in the manner of an expanding floatation zone to combine liquid segments which reside to either side of an air segment in each of the sample liquid test packages upon the initial flow of the test package therethrough in what will hereinafter be termed the "downstream" direction, namely the flow direction to the right as seen in drawing FIG. 1 from the shear valve 130 to and through the flow cell 138 and the vanish zone 140. More specifically, it may be understood that the vanish zone 140 is specifically dimensioned in accordance with the volume of at least one of the sample liquid test package air segments, or vice versa, to prevent the occlusion of that zone by that air segment, thus in essence floating that air segment in liquid therein and combining the liquid segments, for example those of sample liquid S and reagent liquid R1, and that of reagent liquid R2, which reside to either side of that air segment in a sample liquid test package upon the initial flow of the same through the vanish zone 140 in the downstream direction in analytical line 134, all in the manner described in detail hereinbelow.

The detecting means 30 comprise a light source as indicated at 142 of appropriate wavelength, and optically compatible light-sensitive detector as indicated at 144, respectively operatively disposed as shown to opposite sides of the flow cell 138. Optical fibres of appropriate light transmission characteristics are indicated at 146 and 148, and are operatively disposed as shown relative to light source 142, flow cell 138 and detector 144, respectively, to function in conventional colorimetric manner to transmit light from source 142 through flow cell 138 to detector 144 for repeated quantitative analyses of the successive sample liquids of the sample liquid test packages in turn, again as described in greater detail hereinbelow.

Further included in the detecting means 30 of FIG. 1 is a bubble detector as indicated at 150, and taking for example the form of that disclosed in U.S. Pat. No. 4,253,846 issued Mar. 3, 1981 to William J. Smythe, et al, and assigned to the predecessor in interest of the assignee hereof, the disclosure of which is hereby incorporated by reference in this specification. Bubble detector 150 is operatively associated with analytical line 134 immediately upstream of flow cell 138, to detect the passage of the leading edges of the liquid segments in the respective sample liquid test packages and signal the detector 144 accordingly as indicated along line 152.

Figure 2A:
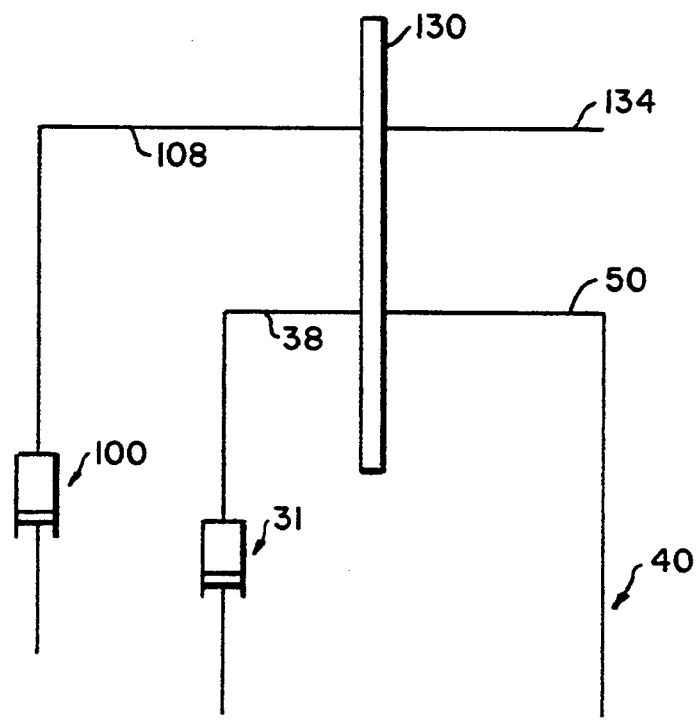
FIGS. 2A and 2B are respectively somewhat simplified schematic diagrams illustrating the two operational conditions of the sample liquid test package transfer means of the system of FIG. 1.
Figure 2B:
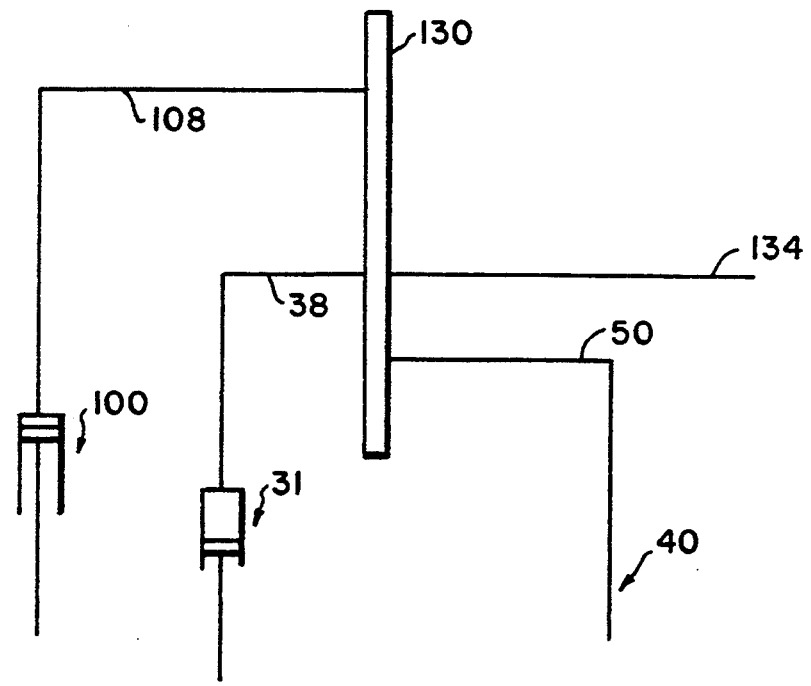

With further regard to the respective aspirate and transfer positions of two position linear shear valve 130 of the test package transfer means 24 of FIG. 1, and with the analytical line 134 of test package reaction and analysis means 28 now having been structurally described in detail in relation thereto, reference may now be had to drawing FIGS. 2A and 2B; with the former schematically depicting the conduit connections effected with the shear valve 130 in the aspirate position, and the latter schematically depicting those conduit connections with the valve in the transfer position.

Figure 3:
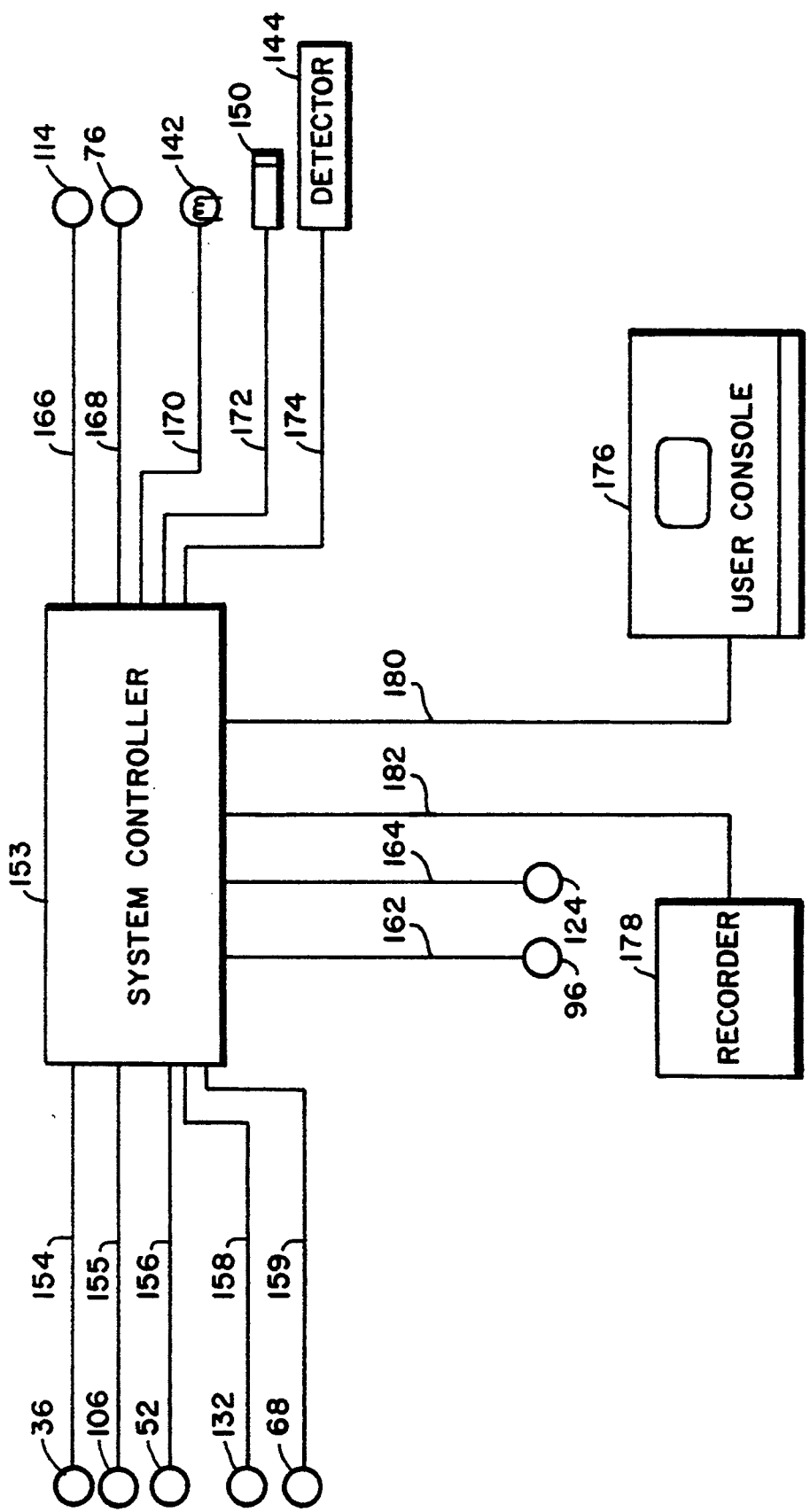
FIG. 3. is a block diagram illustrating the control and synchronization of the electrically operated drive and detection components of the system of FIG. 1.

Referring now to FIG. 3 of the application drawings, the same will be seen as a block diagram schematically illustrating the control and synchronization of the electrically operated components of the system 20 of FIG. 1; and, to that effect, depicts a controller as indicated at 153 taking the form of any appropriately programmable microprocessor device, for example a general purpose digital computer with a stored system program. Controller 153 is operatively connected as indicated by lines 154, 155 and 156 to pump drive motors 36 and 106, and probe assembly drive motor 52, to control and synchronize the respective operations thereof, and thus of pumps 31 and 100; and is operatively connected as indicated by line 158 to shear valve drive motor 132 to like purposes with regard to the operation of shear valve 130. Controller 153 is also operatively connected as indicated by line 159 to sample liquid supply drive motor 68 to control and synchronize the indexing of the sample liquid containers in turn to probe assembly 40; and is operatively connected as indicated by lines 160, 162 and 164 to isolation liquid supply pump, drive motors 94, 96 and 124 to control isolation liquid supply to conduit 108 and probe assembly 40. Controller 153 is also operatively connected as indicated by lines 166 and 168 to vent valve drive motor 114 and isolation liquid supply valve drive motor 76 to control and synchronize the venting of pump 100 to atmosphere, and the supply of isolation liquid to pump 31 and thus to conduit 38; and is also operatively connected to light source 142, bubble detector 150 and detector 144 as indicated by lines 170, 172 and 174 to control and coordinate the respective functions thereof. User console including a standard CRT terminal and keyboard, and a recorder including a standard printer for permanent recording of the sample liquid analysis results, are shown at 176 and 178 in drawing FIG. 3, and are respectively operatively connected as indicated by lines 180 and 182 to the controller 153 for user control of the system 20, and observation and recording of the sample liquid analysis results. Thus, controller 153 may be understood to be effective to instruct, control, monitor, and synchronize the operations of system 20 as described in detail hereinbelow, and to calculate and monitor the sample liquid analysis results and output the same in a variety of formats, all of course in accordance with appropriate programming of the controller 153.

In accordance with the teachings of the herein-disclosed best mode of the system 20 of our invention, pump drive motors 36 and 106, and probe assembly drive motor 52 of FIG. 1 take the form of precisely operable stepping motors which, in accordance with appropriate programming of system controller 153 of FIG. 3 and control of those drive motors as described along lines 154, 155 and 156 of FIG. 3, can be operated to drive pump pistons 34 and 104 of pumps 31 and 100 through different and readily adjustable strokes in pump cylinders 32 and 102, and to drive probe assembly 40 through different and readily adjustable ranges of vertical and horizontal travel relative to the respective sample, reagent and buffer liquid containers, as described in detail hereinbelow.

Figure 4:
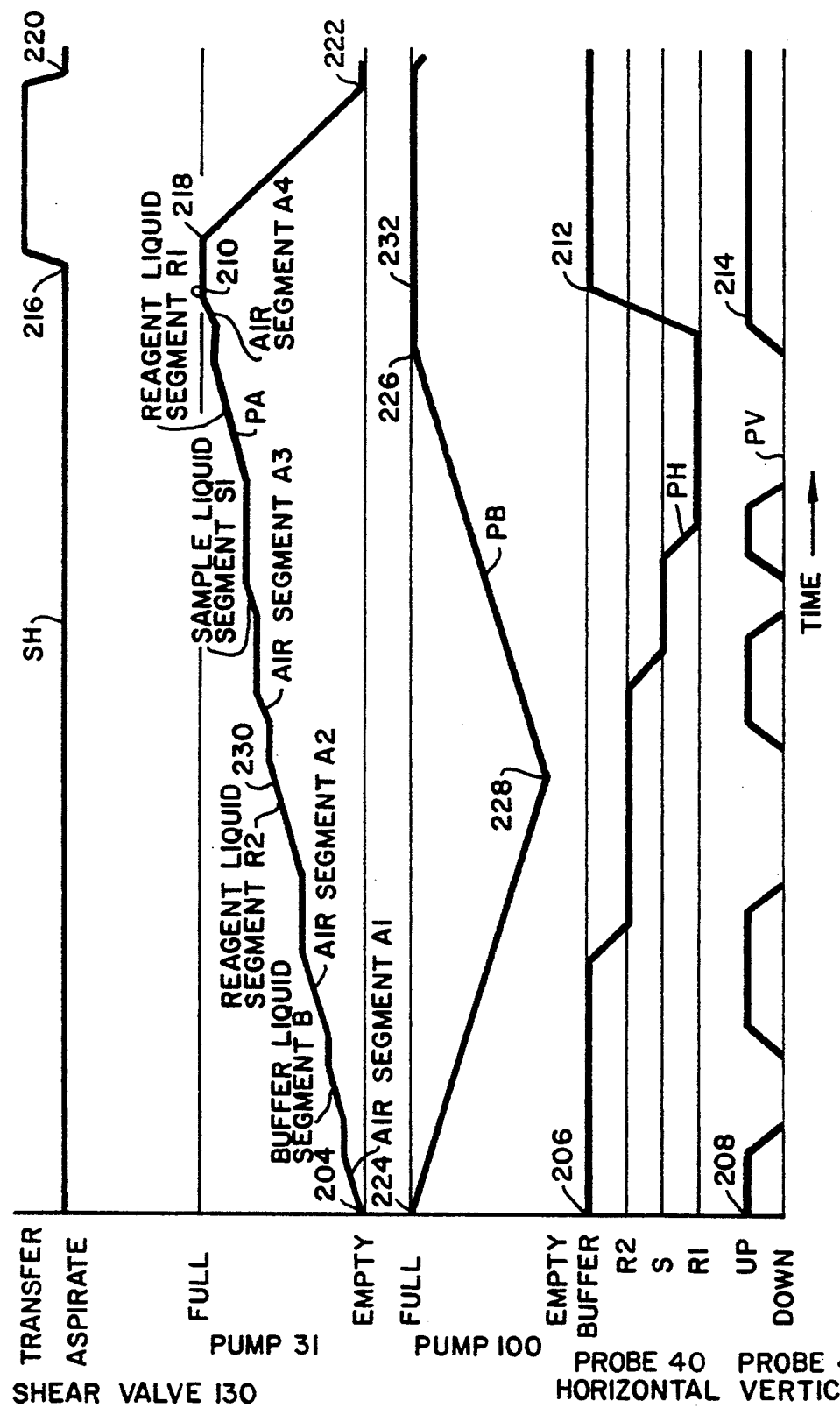
FIG. 4 is a timing diagram illustrating the operations of the sample liquid test package transfer means, and the sample liquid test package metering and supply means, respectively, of the system of FIG. 1 as drawn to the same time scale.

FIG. 4 is a timing diagram illustrating the operational conditions of shear valve 130, pumps 31 and 100, and probe assembly 40 during a representative operational cycle of the system 20 of our invention. To this effect, line SH illustrates the respective aspirate and transfer conditions of shear valve 130, line PA illustrates the position of piston 34 in cylinder 32 of pump 31, line PB illustrates the position of piston 104 in cylinder 102 of pump 100, line PH illustrates the horizontal position of probe assembly 40 relative to the respective sample, reagent and buffer liquid containers, and line PV illustrates the vertical position of probe assembly 40 relative to those containers; it being clear all lines on FIG. 4 are drawn to the same time scale as indicated thereon.

Figure 5:
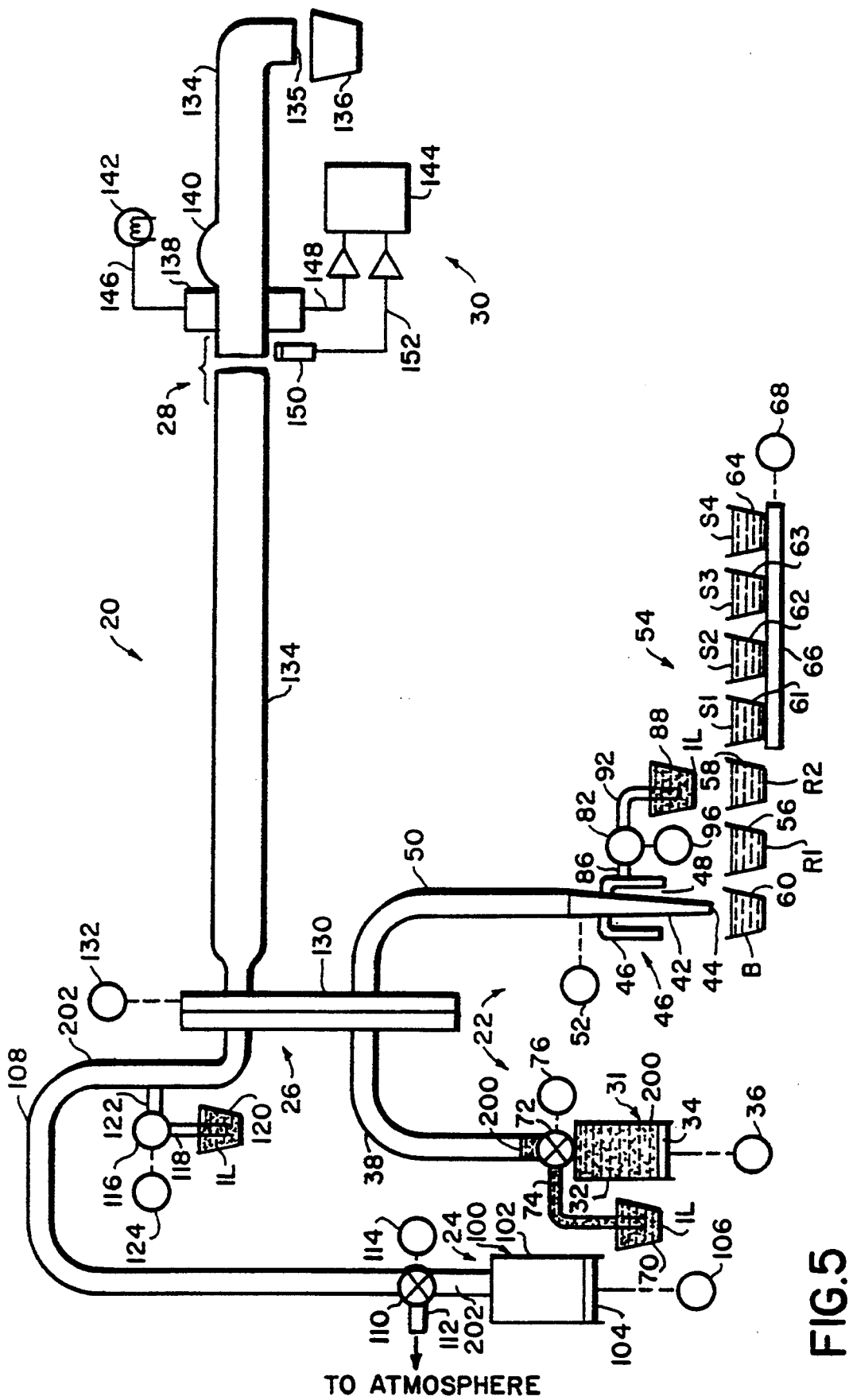
FIGS. 5, 6, 7, 8, 9, 10, 11, 12 and 13 are respectively schematic system diagrams in the nature of FIG. 1 illustrating the operational configurations of the system components at various sequential stages in the initialization of the system and formation of the sample liquid test package stream.

With the respective components of the system 20 of our invention configured and operatively associated as heretofore described, it may be understood that, prior to sample liquid test package supply and analysis, the system is initialized to provide respective volumes or columns of the isolation liquid IL and ambient air above pump pistons 34 and 104 to in essence act as extensions of those pistons in the performance of the pumping functions, thereby preventing any contact by the sample liquid test packages with pump 31 and valve 72, and pump 100, and totally preventing sample liquid carryover in those otherwise highly carryover-intensive system components. More specifically, and with shear valve 130 in the aspirate position thereof of FIG. 2A to connect conduits 38 and 50 therethrough, with valve 72 operated by drive motor 76 to connect pump cylinder 32 to isolation liquid reservoir 70 through conduit 74, and with pump piston 34 driven by drive motor 36 essentially to the top of pump cylinder 32, pump piston 34 is then driven by drive motor 36 essentially to the bottom of pump cylinder 32 thereby aspirating the isolation liquid IL from reservoir 70 thereinto through conduit 74 and substantially filling pump cylinder 32 with the same. Valve 72 is then operated by drive motor 76 to connect pump cylinder 32 to conduit 38, thereby leaving pump cylinder 32 substantially filled with the isolation liquid IL, with any air which was entrapped below the isolation liquid in the pump cylinder simply flowing under the force of gravity therefrom into conduit 38 by virtue of the connection of the same to atmosphere through the open end 44 of probe tube 42. Pump piston 34 is then driven upwardly to a slight extent by drive motor 36 to the piston position illustrated in drawing FIG. 5 wherein the pump cylinder 32, the valve 72, and a small extent of conduit 38 above the latter are filled with the isolation liquid IL; thereby providing an isolation liquid column as indicated at 200 in FIG. 5 above piston 34 which acts as an extension of the piston for sample liquid test package aspiration and supply to the system 20 as described in detail hereinbelow. This also establishes an operational bottom dead center position for piston 34 in pump cylinder 32. Concomitantly, piston 104 of pump 100 is driven by drive motor 106 to the bottom of pump cylinder 102 as shown in FIG. 5 to establish an operational bottom dead center position for that pump piston; and this results in pump cylinder 102 and conduit 108 being filled with ambient air as drawn thereinto through shear valve 130, analytical line 134, and the open end 135 of the latter. This provides an air column as indicated at 202 in FIG. 5 above piston 104 in pump cylinder 102 and conduit 108 which acts as an extension of that piston for the bi-directional displacement of the sample liquid test packages through the analytical line by pump 100 as described in detail hereinbelow.

Alternatively, air column 202 may be provided by driving three way rotary valve 110 to the second position thereof to connect pump cylinder 102 and the portion of conduit 108 below the valve as seen in FIG. 5 to atmosphere, and the drive as above of pump piston 102 to the operational bottom dead center position thereof to fill pump cylinder with ambient air as drawn in through vent conduit 112; whereupon valve 110 is returned to the first position thereof.

Figure 6:
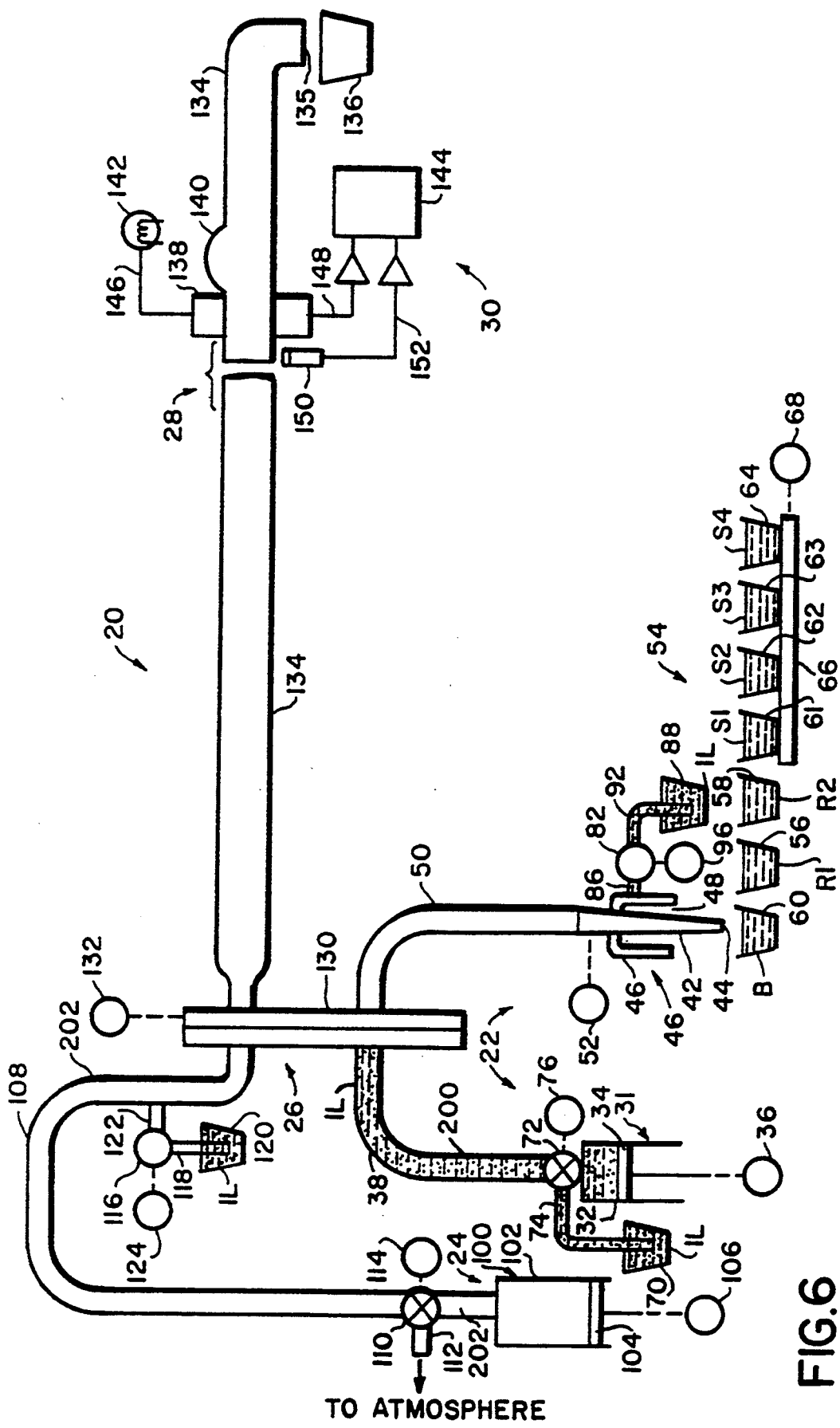

With the shear valve 130 remaining in the aspirate position thereof, pump piston 34 of pump 31 is then driven upwardly by drive motor 36 in pump cylinder 32 to the operational top dead center position thereof as illustrated in drawing FIG. 6 which, in accordance with the desired overall volume of the sample liquid test packages to be aspirated may, for example, be approximately two thirds of the way to the top of pump cylinder 31 as shown; and this results in the isolation liquid column 200 above the piston 34 being displaced in conduit 108 essentially to the upstream side of the shear valve 130, with the ambient air ahead of that column being simply displaced to atmosphere through the connected conduit 50, probe tube 42, and the open end 44 of the latter. This will also result in a small quantity of the isolation liquid being drawn by capillarity and gravity to flow along with the air through shear valve 130 into and through conduit 50 and probe tube 42 to coat the inside surfaces thereof with an initial layer of the isolation liquid.

Pump piston 34 is then intermittently driven downwardly by drive motor 36 to return to the operational bottom dead center position thereof of FIG. 5. Concomitantly, and with isolation liquid pumps 82 driven by drive motor 96 to supply isolation liquid IL as required from isolation liquid reservoir 88 to the exterior surface of probe tube 42 to form an isolation liquid layer thereon, and with an isolation liquid layer formed on the interior surfaces of conduit 50 and probe tube 42, both as heretofore described, and with sample liquid container 61 containing sample liquid S1 indexed on transport device 66 by drive motor 68 into operable position relative to the open end 44 of probe tube 42, the probe assembly 44 is operated by drive motor 52 to, in seriatim, leave the open probe tube end 44 exposed to the ambient air to aspirate a first air segment A1 thereinto, immerse the open probe tube end in container 60 of the buffer liquid B to aspirate a buffer liquid segment B thereinto, again expose the open probe tube end to the ambient air to aspirate a second air segment A2 thereinto, immerse the open probe tube end in container 58 of reagent liquid R2 to aspirate a segment R2 of that reagent liquid thereinto, again expose the open probe tube end to the ambient air to aspirate a third air segment A3 thereinto, immerse the open probe tube end in container 61 of sample liquid S1 to aspirate a segment S1 of the sample liquid thereinto, immerse the open probe tube end in container 56 of reagent liquid R1 to aspirate a segment R1 of that reagent liquid thereinto for immediate merger with the reagent liquid segment R1 within the probe tube 42, and again expose the open probe tube end to the ambient air to aspirate a fourth air segment A4 thereinto, respectively. These concomitant operations as described of pump 31 and probe assembly 40 are clearly illustrated by lines, PA, PH and PV of the timing diagram of drawing FIG. 4, commencing respectively at time-coincident points 204, 206 and 208 on lines PA, PH and PV, and ending respectively at points 210, 212 and 214 on those timing diagram lines, which are also time-coincident. As made clear by the appropriately labelled segments of line PA of the timing diagram of FIG. 4, and by the horizontal line segments which are of course indicative of temporary cessation of downward pumping motion of pump piston 34, nothing is aspirated by probe tube 42 intermediate the aspiration of the respective air and buffer liquid segments A1 and B, intermediate the aspirations of the respective buffer liquid and air segments B and A2, intermediate the respective aspirations of air and reagent liquid segments A2 and R2, intermediate the aspirations of the respective reagent liquid and air segments R2 and A3, intermediate the aspirations of the respective air and sample liquid segments A3 and S1, and intermediate the aspirations of the respective sample liquid and reagent liquid segments S1 and R1; with the latter of course resulting in the merger of the sample and reagent liquid segments S1 and R1 in the probe tube 41 as heretofore described.

Concomitantly with the aspirations as described into probe tube 42 of the respective sample, buffer and reagent liquid segments S1, B, R1 and R2, and separating air segments A1, A2, A3 and A4, it will be understood by those skilled in this art that some portion of the isolation liquid IL supplied as heretofore described to the annular exterior surface of probe tube 42 by pump 82 to coat that surface with an isolation liquid layer will flow down the same under the force of gravity to the probe tube tip for aspiration into the open probe tube end 44 with each of those liquid and air segments, thereby replenishing and maintaining the sample liquid carryover-minimizing isolation liquid layer on the interior surface of the probe tube 41.

Figure 7:
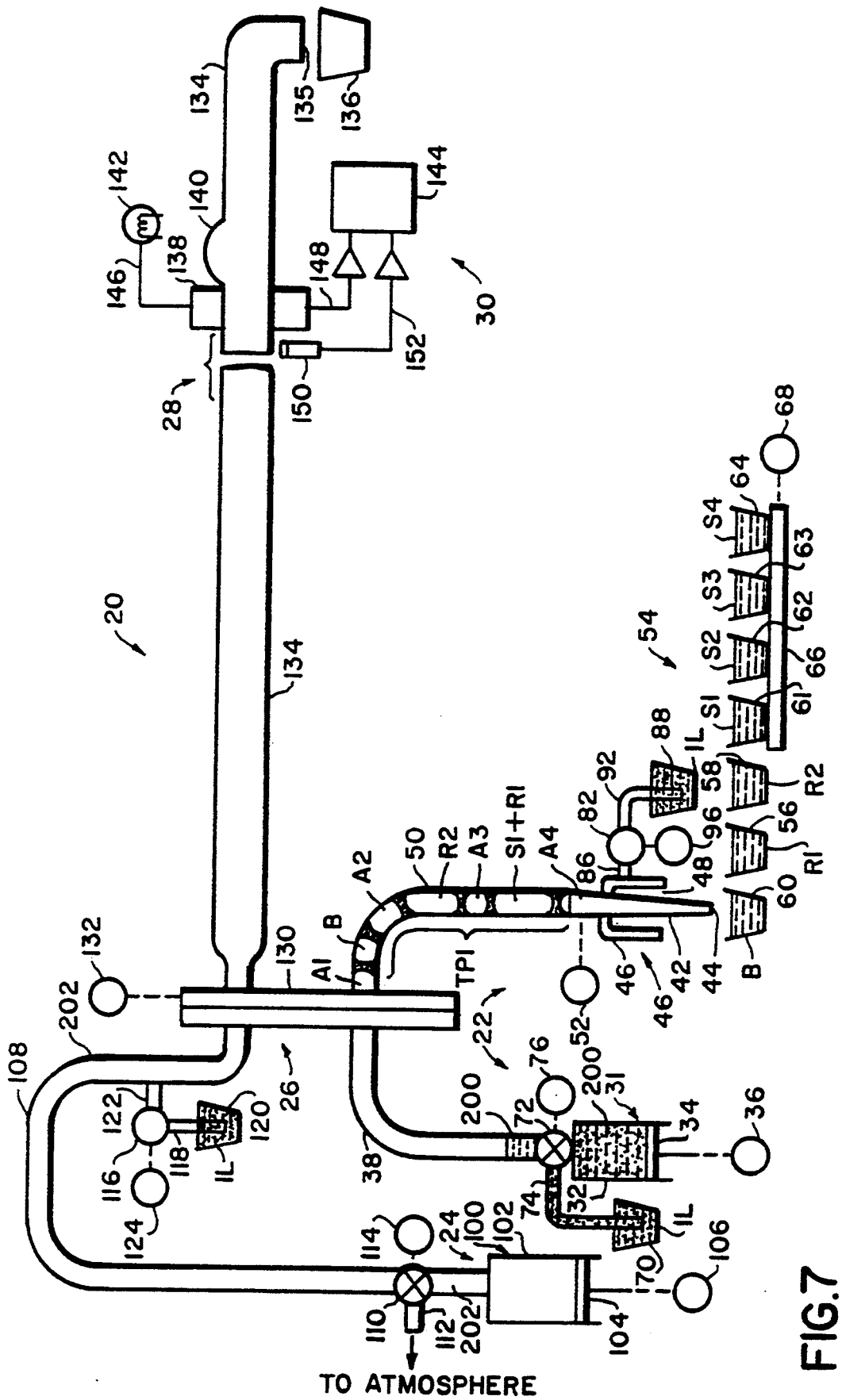

All of the above results in the formation of a first sample liquid test package as indicated at TP1 in drawing FIG. 7, and the aspiration thereof by pump 31 from probe tube 42 into conduit 50 essentially to the downstream side of the shear valve as shown in FIG. 7; with sample liquid test package TP1 comprising serially arranged, merged sample and reagent liquid segment S1+R1, separating air segment A3, reagent liquid segment R2, separating air segment A2, and buffer liquid segment B, respectively, and further including and being bracketed as shown to both the upstream and downstream sides by separating air segments A1 and A4. In accordance with operation of probe assembly isolation liquid supply pump 82 attendant formation as described of sample liquid test package TP1, it may be understood that all liquid and separating air segments of that sample liquid test package will be fully encapsulated as shown in FIG. 7 in layers of the isolation liquid IL in the manner described in detail in U.S. Pat. 4,121,466 referenced hereinabove; and all of course to particularly effective purpose with regard to the minimization of sample liquid carryover.

With further regard to sample liquid test package TP1, it may be understood that, through appropriate programming of system controller 153 which controls the operations as described of probe assembly 40 and pump 31 as heretofore described with reference to drawing FIG. 3, the volume of test package separating air segment A3 is specifically determined in accordance with the known volume of the vanish zone 140 of analytical line 134 to prevent separating air segment A3 from occluding that vanish zone upon the flow of the test package therethrough, all as described in detail in U.S. Pat. 4,853,336 referenced. hereinabove.

Although as made clear by drawing FIG. 7 there are as yet no sample liquid test packages resident in analytical line 134, isolation liquid supply pump 116 may be driven by drive motor 124 to supply isolation liquid IL from reservoir 120 through conduits 118 and 122 to conduit 108, and pump 100 driven by drive motor 106 through a complete cycle of operation as illustrated by line PB in the timing diagram of drawing FIG. 4, both concomitantly with the formation of sample liquid test package TP1 as described. This will result in the isolation liquid IL in conduit 108 being picked up by the column of air 202 as the same is moved by pump piston 104 through shear valve 130 into the connected analytical line 134 on the upward stroke of pump piston 104, and the deposition of at least some of the isolation liquid IL on the interior wall of the analytical line 134 despite the return of the air column 202 to the upstream side of the shear valve 130 as pump piston returns to the bottom dead center position thereof as shown in FIG. 7.

Figure 8:
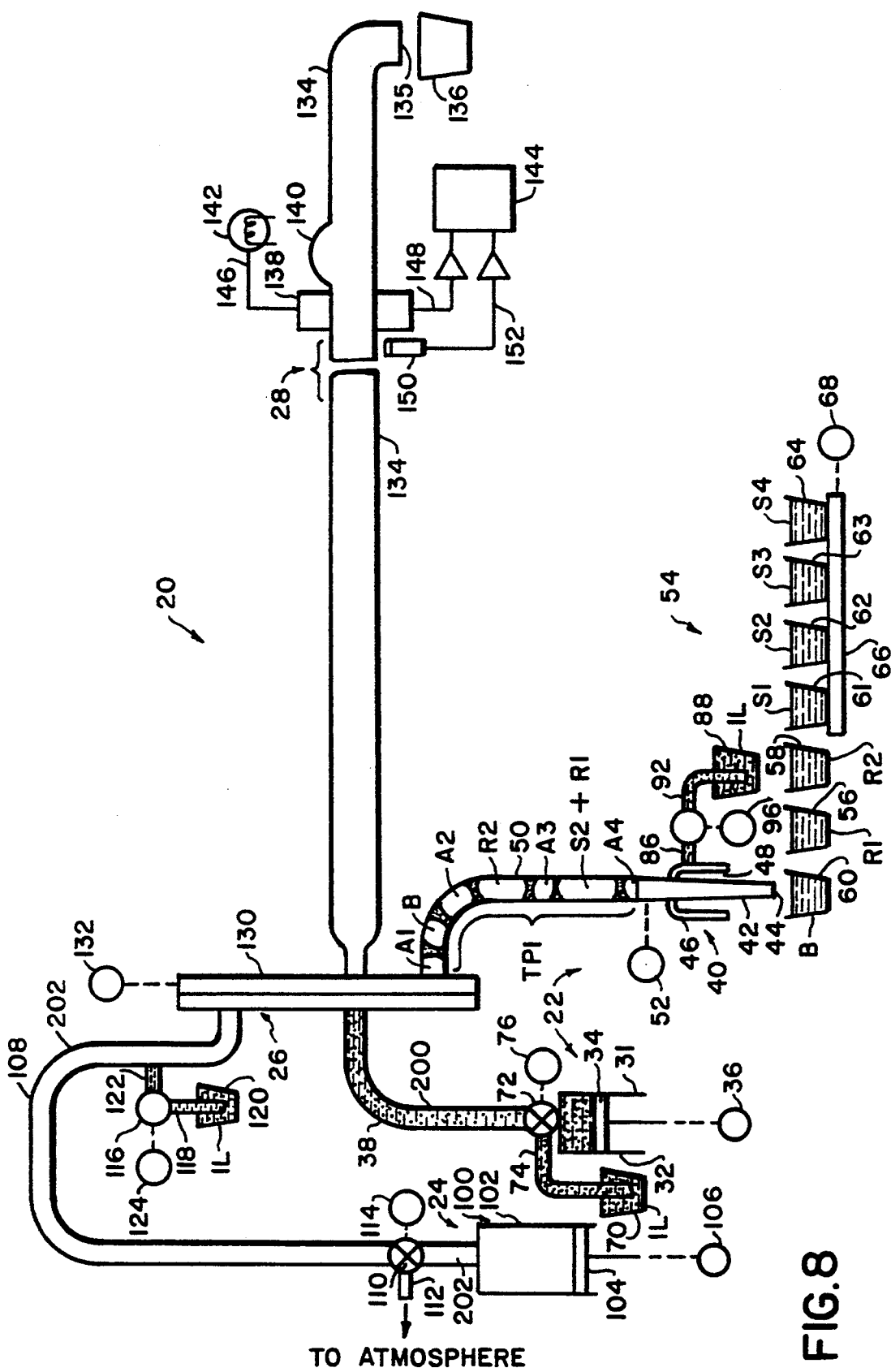

Following formation as described of sample liquid test package TP1, shear valve 130 is driven by drive motor 132 to the transfer position thereof of FIG. 2B to connect conduit 38 to the analytical line 134, while simply sealing off conduits 50 and 108 at the shear valve. Piston 34 of pump 31 is then driven by drive motor 36 to return to the operational top dead center position thereof in cylinder 32; and this results in the column 200 of isolation liquid IL above pump piston being again driven essentially to the upstream side of shear valve 130, with the air ahead of the same in conduit 38 and connected analytical line 134 being simply driven to atmosphere through the open end 135 of the latter, and with sample liquid test package TP1 simply remaining resident in conduit 50 which is now sealed off at the downstream face of the shear valve 130, thus bringing the system 20 of our invention to the operational condition thereof depicted in FIG. 8.

Figure 9:
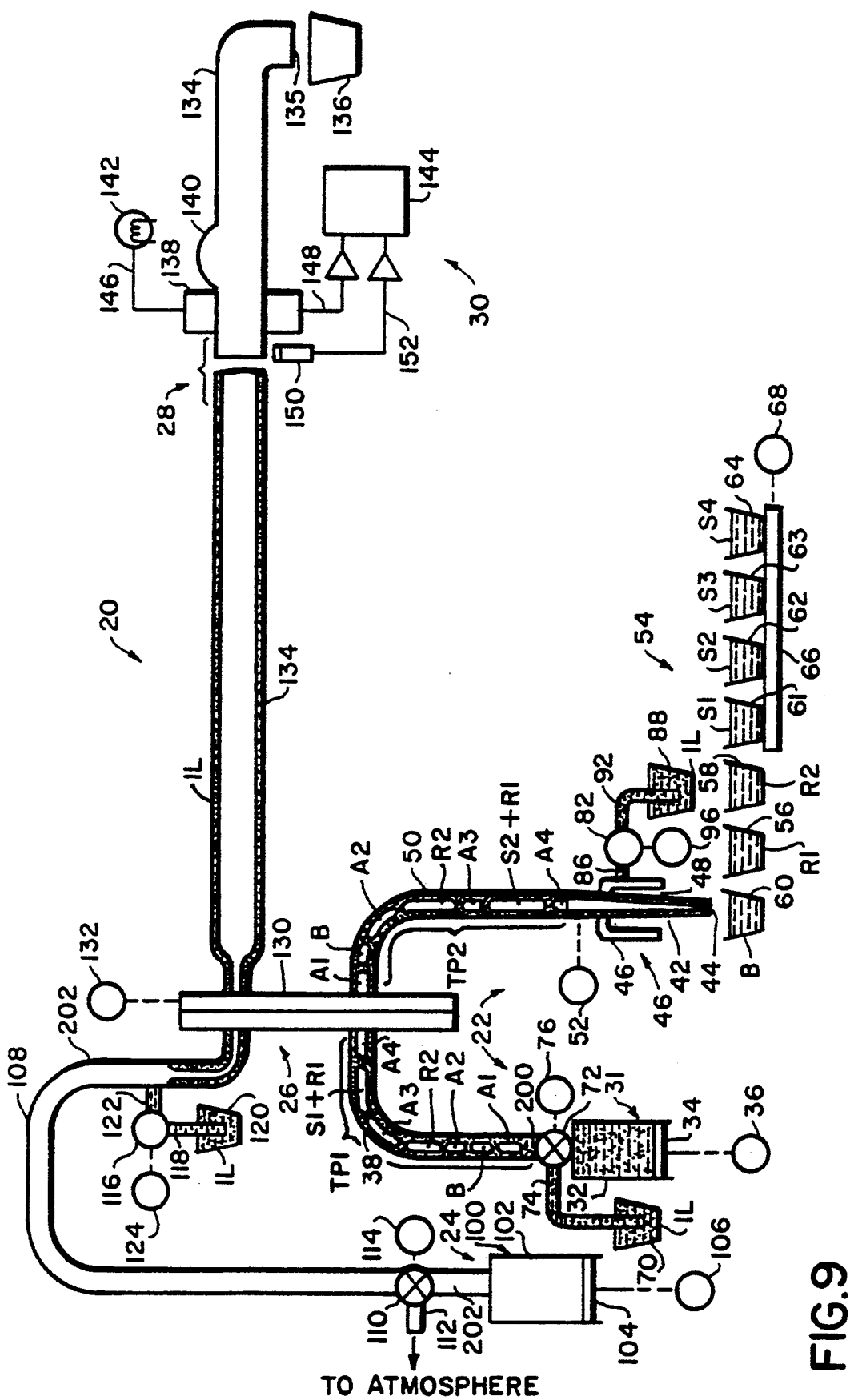

The shear valve 130 is then driven by drive motor 132 to return to the aspirate position thereof, and sample liquid container 62 containing sample liquid S2 is indexed on transport device 66 by drive motor 68 into position for access by probe tube 42. Piston 34 of pump 31 is then driven by drive motor 36 to the operational bottom dead center position thereof, and probe assembly 40 concomitantly actuated as heretofore described relative to sample liquid container 62, and the respective buffer liquid B and reagent liquids R1 and R2 containers 60, 56 and 58, whereupon aspiration as heretofore described of a second sample liquid test package TP2 by pump 31 through probe tube 40 into conduit 50, and resultant displacement of the previously aspirated sample liquid test package TP1 from conduit 50 through shear valve 130 into conduit 38, are accomplished; thereby bringing the system 20 of our invention to the operational condition depicted in application drawing FIG. 9. As this occurs, pump 100 may again be cycled through one complete stroke, and pump 116 operated as required, for supply of further isolation liquid IL from isolation liquid reservoir 120 as heretofore described through shear valve 130 to the interior surface of the now connected, but still empty insofar as sample liquid test packages are concerned, analytical line 134.

Figure 10:
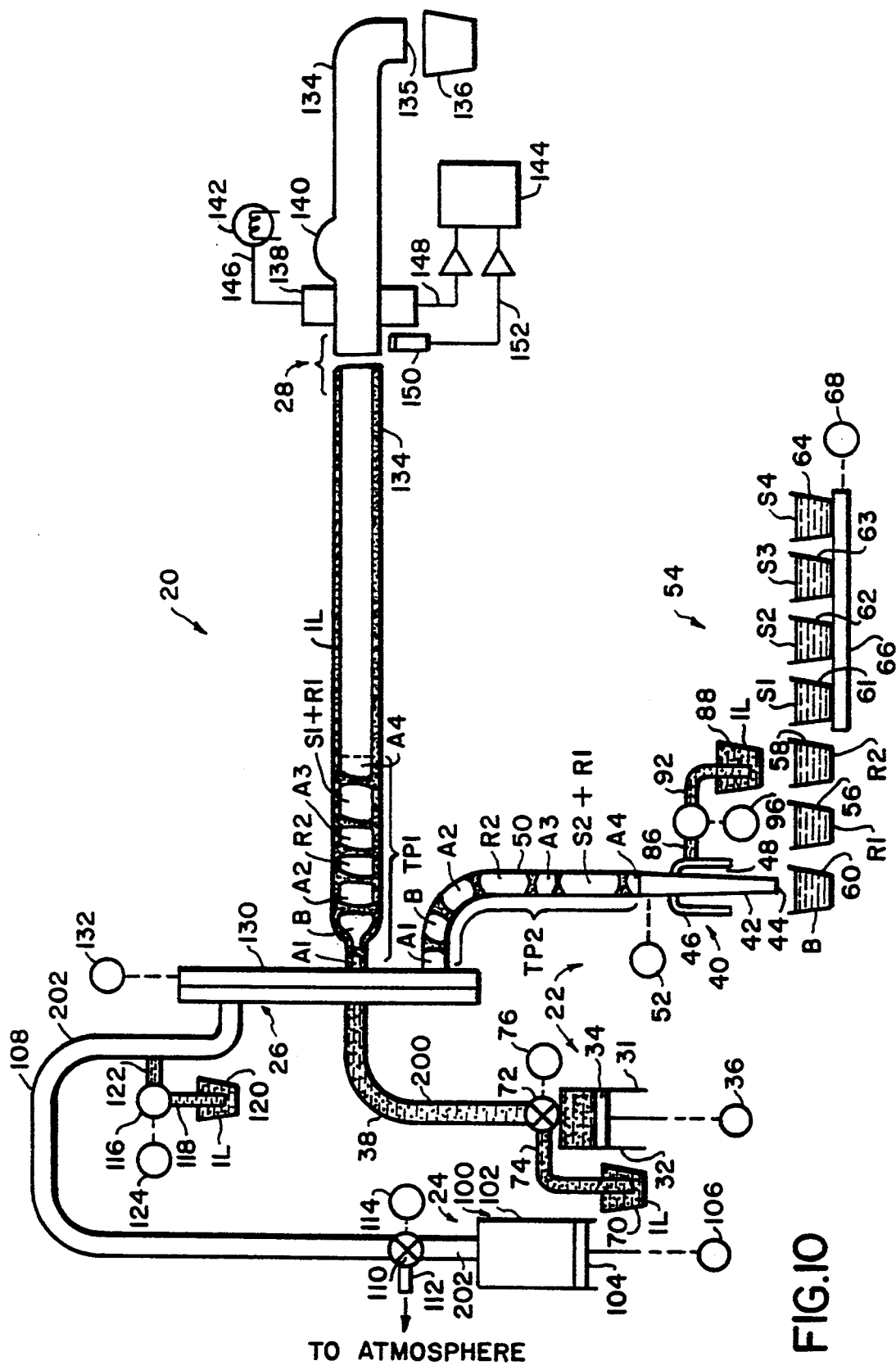

The shear valve 130 is then again driven by drive motor 132 to the transfer position thereof, and piston 34 of pump 31 then driven by motor 36 to return to the operational top dead center position thereof; and this results in the sample liquid test package TP1 being transferred as shown in drawing FIG. 10 by the pumping action of the column 200 of isolation liquid IL above pump piston 34 from conduit 38 through shear valve 130 to the now connected analytical line 134 at the downstream side of the shear valve, while leaving sample liquid test package TP2 still resident as shown in conduit 50. The shear valve 130 is then returned to the aspirate position thereof by drive motor 132 to re-connect conduits 38 and 50, and conduit 108 and the analytical line 134; thereby returning the operative components of the system 20 to the respective conditions thereof depicted in FIG. 6, but leaving the sample liquid test package TP1 resident as shown in FIG. 10 in the analytical line 134 immediately downstream of the shear valve 130. These operations of the shear valve 130 and pump 31 are clearly illustrated by lines SH and PA of the timing diagram of drawing FIG. 4, commencing respectively at points 216 and 218, which are not time coincident, on lines SH and PA, and ending respectively at points 220 and 222, which are time coincident, on those lines. Lines PB, PH and PV of FIG. 4 make clear that pump 100 and probe assembly 40 do not operate during this sample liquid test package transfer procedure.

Sample liquid container 63 containing sample liquid S3 is then indexed on transport device 66 by drive motor 68 into position for access by probe tube 42, whereupon aspiration as heretofore described of a third sample liquid test package TP3 by pump 31 through probe tube 40 into conduit 50 at the downstream side of the shear valve is accomplished, with resultant displacement of the previously aspirated sample liquid test package TP2 from conduit 50 through the shear valve 130 into conduit 38 then also occuring. Concomitantly, piston 104 of pump 100 is driven through one complete stroke as illustrated by line PB in FIG. 4 and extending from points 224 to 226 thereon to, in accordance with the resultant bi-directional displacement of the column of air 202 in conduit 108 above piston 104, bi-directionally displace sample liquid test package TP1 in analytical line 134; first to the right in the analytical line 134 as seen in the application drawings to a distance determined by the ratio between the displacement of the pump 100 and the cross-sectional area of the analytical line 134, and then to the same distance to the left to return the sample liquid test package TP1 essentially to its starting position immediately at the downstream side of the shear valve 130. The respective operational conditions of the system 20 intermediate this step, and at the completion thereof, are illustrated by FIGS. 11 and 12 of the application drawings: with FIG. 11 illustrating the same at the time when sample liquid test package TP1 has reached the right-most limit of its initial displacement by pump 100 in analytical line 134 which is indicated by point 228 on line PB in the timing diagram of FIG. 4, and aspiration of sample liquid test package TP3 into conduit 50, and displacement by the same of sample liquid test package TP2 from conduit 50 through shear valve 130 into conduit 38 by pump 31 are at intermediate stages as indicated by time coincident point 230 on line PA in FIG. 4; and FIG. 12 illustrating operational system conditions upon the return of sample liquid test package TP1 in analytical line 134 essentially to the downstream side of the shear valve 130, and the completion of the aspiration and supply of sample liquid test package TP3 to conduit 38 and the displacement of sample liquid test package TP2 into conduit 38, as respectively indicated by time-coincident points 210 and 232 on lines PA and PB in FIG. 4.

Figure 11:
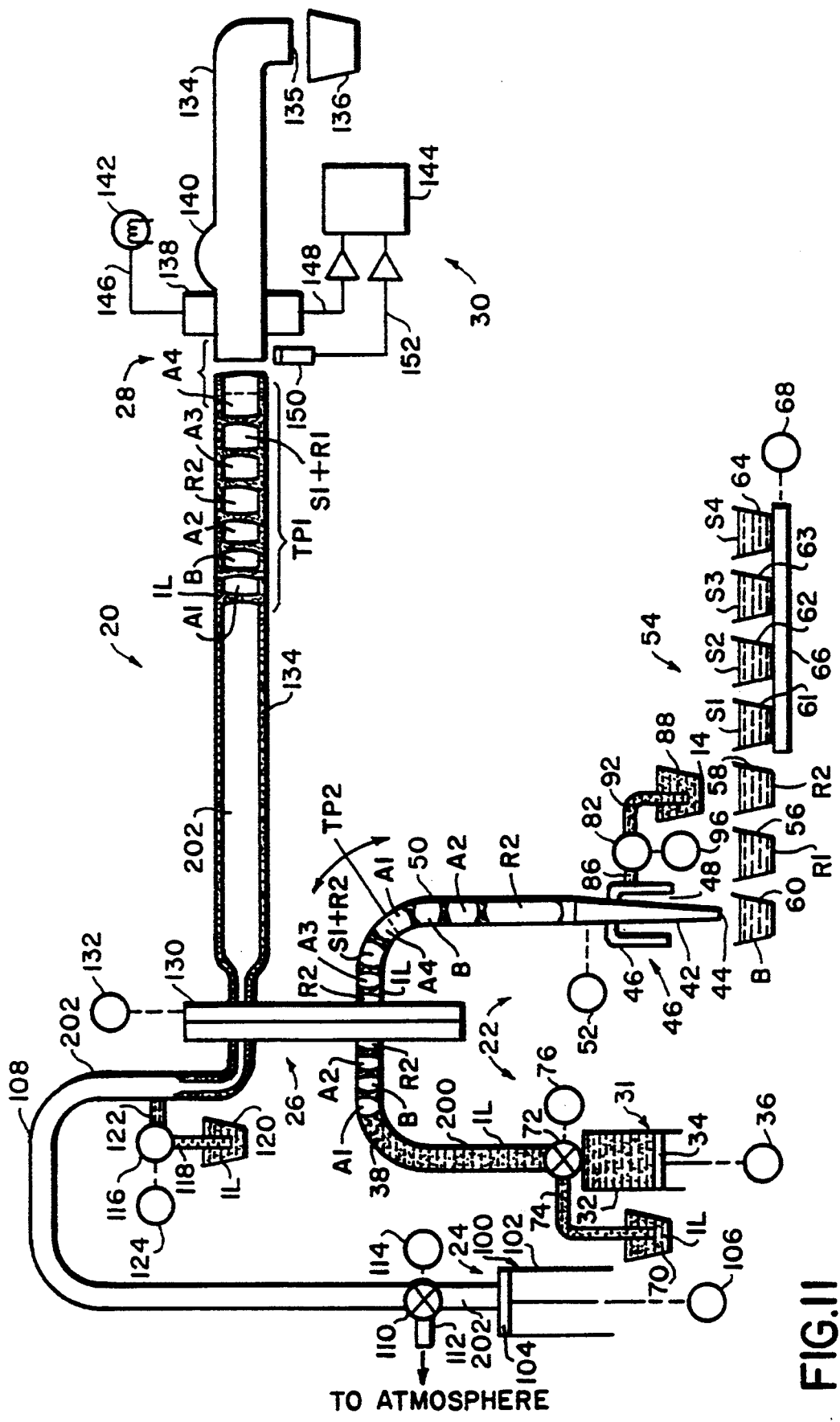

FIG. 11 makes clear that the initial displacement as described of sample liquid test package TP1 to the right by pump 100 is not of sufficient extent to cause any part of that test package to flow through flow cell 138 into the vanish zone 140 in analytical line 134; although it will be immediately understood by those skilled in this art that the bi-directional displacement as described of the isolation liquid-encapsulated sample liquid test package TP1 in analytical line 134, coupled with the concomitant supply of additional isolation liquid IL from reservoir 120 to analytical line 134 by pump 116 through conduits 122 and 108 and the shear valve 130 attendant operation as described of pump 100, will be effective to form or replenish, as the case may be, a sample liquid carryover-minimizing layer of the isolation liquid on the internal wall of the analytical line 134, at least coincident at this operational stage of the system 20 with the right-most extent of sample liquid test package displacement in the analytical line; and this layer of the isolation liquid IL is illustrated as such in drawing FIG. 10.

Figure 13:
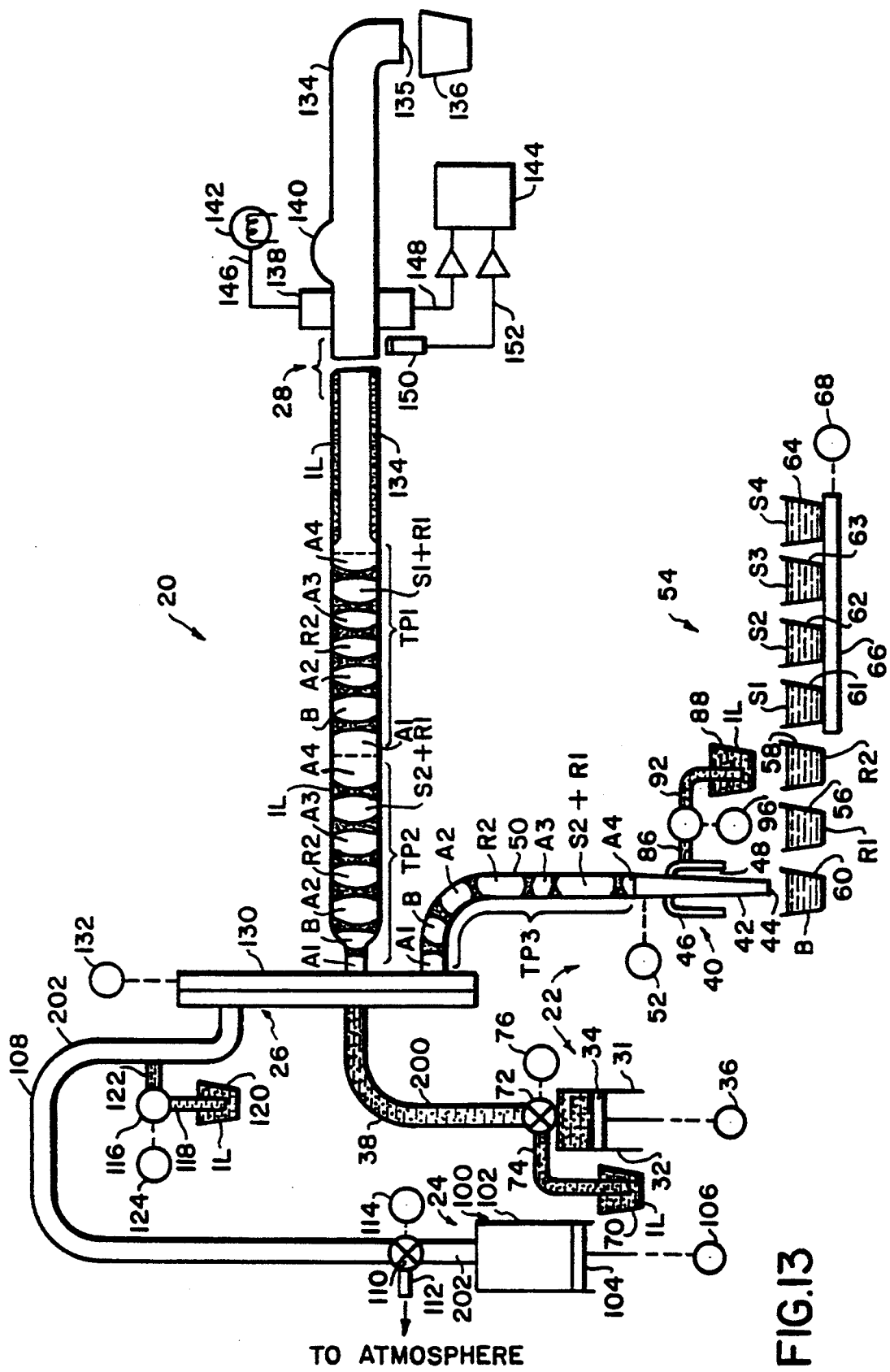

Shear valve 130 is then driven by drive motor 132 to the transfer position thereof, and piston 34 of pump 31 driven by drive motor 36 to the operational top dead center position thereof, thus resulting in the transfer of sample liquid test package TP2 from conduit 38 through the shear valve into the connected analytical line 134 immediately upstream of the previously transferred sample liquid test package TP1; and this brings the system 20 of our invention to the operational condition depicted in drawing FIG. 13 wherein the formation of sample liquid test package stream, consisting at this point in time of sample liquid test packages TP1 and TP2, has now been commenced; it being clear that injection as described of sample liquid test package TP2 into the analytical line 134 has operated to in essence index sample liquid test package TP1 a distance to the right in the analytical line equal to the longitudinal extent of a sample liquid test package, including the leading and trailing separating air segments A1 and A4, in the analytical line 134 as seen in FIG. 11. For convenience of description, this distance will hereinafter be referred to as a "test package distance." Sample liquid test package TP3 simply remains resident in conduit 50 during this operational cycle of pump 31.

Figure 12:
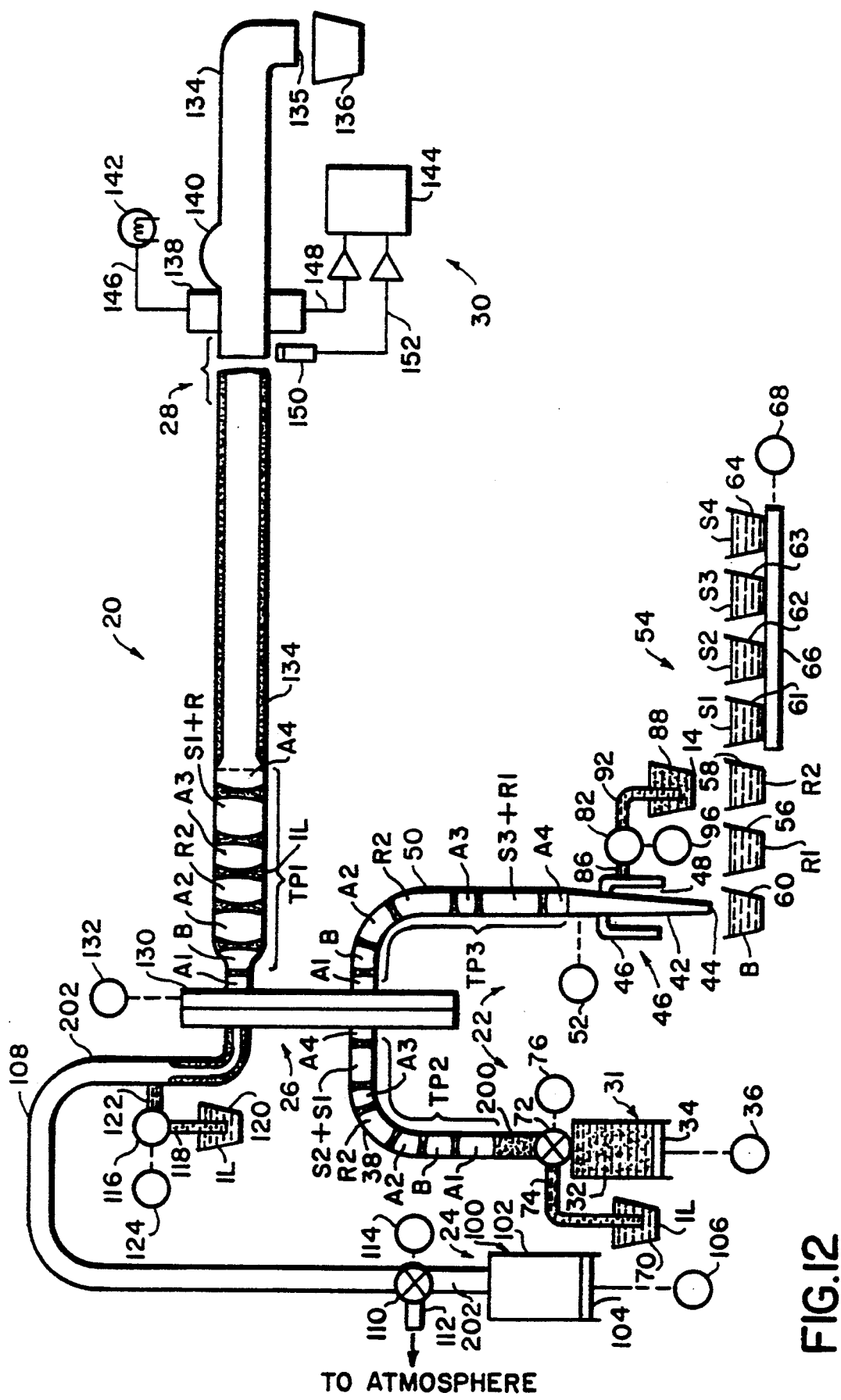

Shear valve 130 is then returned to the aspirate position thereof by drive motor 132, and piston 104 of pump 100 driven by drive motor 106 through one complete stroke thereof to again bi-directionally displace the test package stream of sample liquid test packages TP1 and TP2 in the analytical line 134; first to right as heretofore described with regard to FIG. 11, and to then return the test package stream essentially to the position thereof of FIG. 13 in the manner heretofore described with regard to FIG. 12. However, and since the test package stream now consists of two sample liquid test packages TP1 and TP2, it will be immediately clear to those skilled in this art that the distance to which the leading sample liquid test package TP1 in that stream advances to the right in the analytical line 134 attendant the initial stream displacement in that direction will be increased by one test package distance. In accordance with the hereindisclosed best mode of our invention, it will be understood that this advancement of sample liquid test package TP1 will nonetheless remain insufficient to cause any portion of the same to reach or flow through flow cell 138 or, as must follow, the vanish zone 140. Thus, the integrity of the sample liquid test package stream TP1 continues to remain unaffected by this second bi-directional displacement thereof in analytical line 134.

Operation of the system 20 of our invention continues as described with the succeeding sample liquid test packages being aspirated in turn into conduit 50 by appropriately coordinated actions of sample liquid container transport device 66, probe assembly 40, shear valve 130 and pump 31; displaced in turn from conduit 38 into conduit 50; and transferred in turn from conduit 50 back through the shear valve 130 into the analytical line 134 to, in each instance, add one sample liquid test package to the test package stream in the analytical line and index the latter one test package distance to the right. This results in the sample liquid test package stream being bi-directionally displaced as described in the analytical line 134 by coordinated action of pump 100 and shear valve 130 immediately following the addition of each of the succeeding sample liquid test package in turn thereto.

This repeated bi-directional displacement as described, or what will hereinafter be referred to as "sloshing" of the sample liquid test package stream back and forth in the analytical line 134 will, in accordance with the teachings of our invention, be immediately understood by those skilled in this art to be of highly significant advantage with regard to the overall accuracy of the sample liquid analysis results provided by the system 20. More specifically, this repeated sloshing back and forth in the analytical line of the respective sample and reagent liquid segments S+R1 in each of the test packages in the test package stream results in the particularly thorough and highly effective mixing of those sample and reagent liquids in accordance with the constantly reversing Bolus flow patterns set up therein as a result of the same, thus advantageously promoting to completion in accordance with the time provided therefor as described in detail hereinbelow the requisite sample and reagent liquids S+R1 reactions, totally without need to that effect for highly sample liquid carryover-intensive mixing coil-conduit joints in the analytical line 134. In addition, this elimination of mixing coils from the analytical line 134 operates to significantly reduce hydraulic back pressure in the system 20 to thereby improve the precision of operation thereof insofar as the precise formation and pumping of the sample liquid test package stream are concerned, in particular in view of the compressibility of the respective separating air segments A1, A2, A3 and A4. Further, this repeated sloshing back and forth of the respective sample liquid test packages in the analytical line 134 will cause the included buffer liquid segments B to in essence repeatedly and bi-directionally scrub the layer of isolation liquid IL on the internal wall of the analytical line 134 to remove sample liquid residue therefrom, thus effectively washing the same to even greater minimization of sample liquid carryover; with this scrubbing action of the buffer liquid segments being both physically effective to that end, and chemically effective with regard to recapture of dissolved CO2 as picked up by the isolation liquid layer from a preceding sample liquid segment to prevent the redeposition thereof in a succeeding sample liquid segment. Additionally significant advantages of this sloshing of the test package stream in the analytical line 134 will be made apparent and discussed in detail hereinbelow.

Operation of the system 20 of our invention continues as described, with one sample liquid test package being aspirated from the respective buffer liquid B and reagent liquid R1 and R2 containers, and the sample liquid S4 and succeeding sample liquid containers in turn, and added to the test package stream by the action of pump 31 to advance the same one test package distance to the right in the analytical line 134 for each operational cycle of the system 20, and the test package stream being bi-directionally displaced in the analytical line immediately following each such test package addition thereto by the action of pump 100. Ultimately, and in accordance with the relevant operational parameters of the system 20, this will of course result in the leading sample liquid test package TP1 being bi-directionally displaced in the analytical line 134 to flow twice through the flow cell 138 and the vanish zone 140; first in the direction from left to right as seen in the application drawings, and then in the direction from right to left as seen therein to return essentially to the same position thereof in the analytical line as described.

Figure 14:
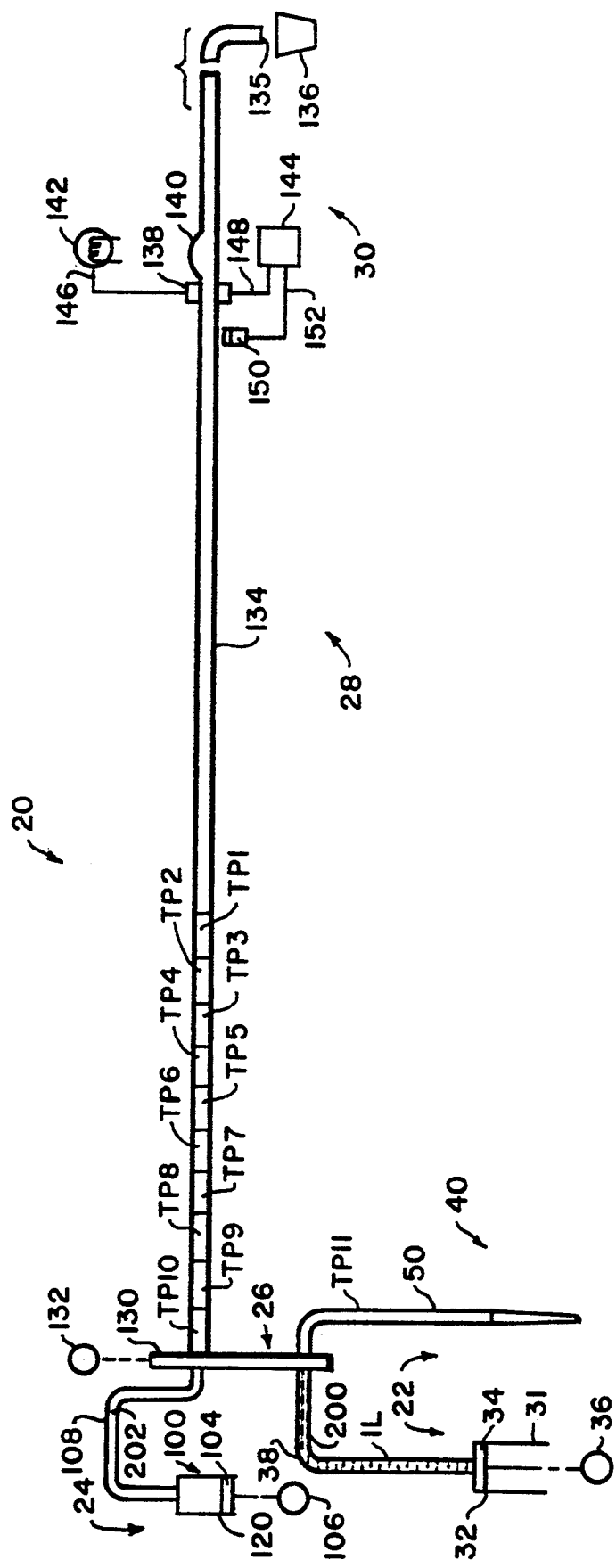
FIGS. 14, 15 and 16 are respectively somewhat simplified schematic diagrams of the system of FIG. 1 illustrating the operational configurations of the basic system components at various later sequential stages in the formation of the sample liquids test package stream, and in the reaction and analysis of the discrete sample liquids as respectively contained therein.
Figure 15:
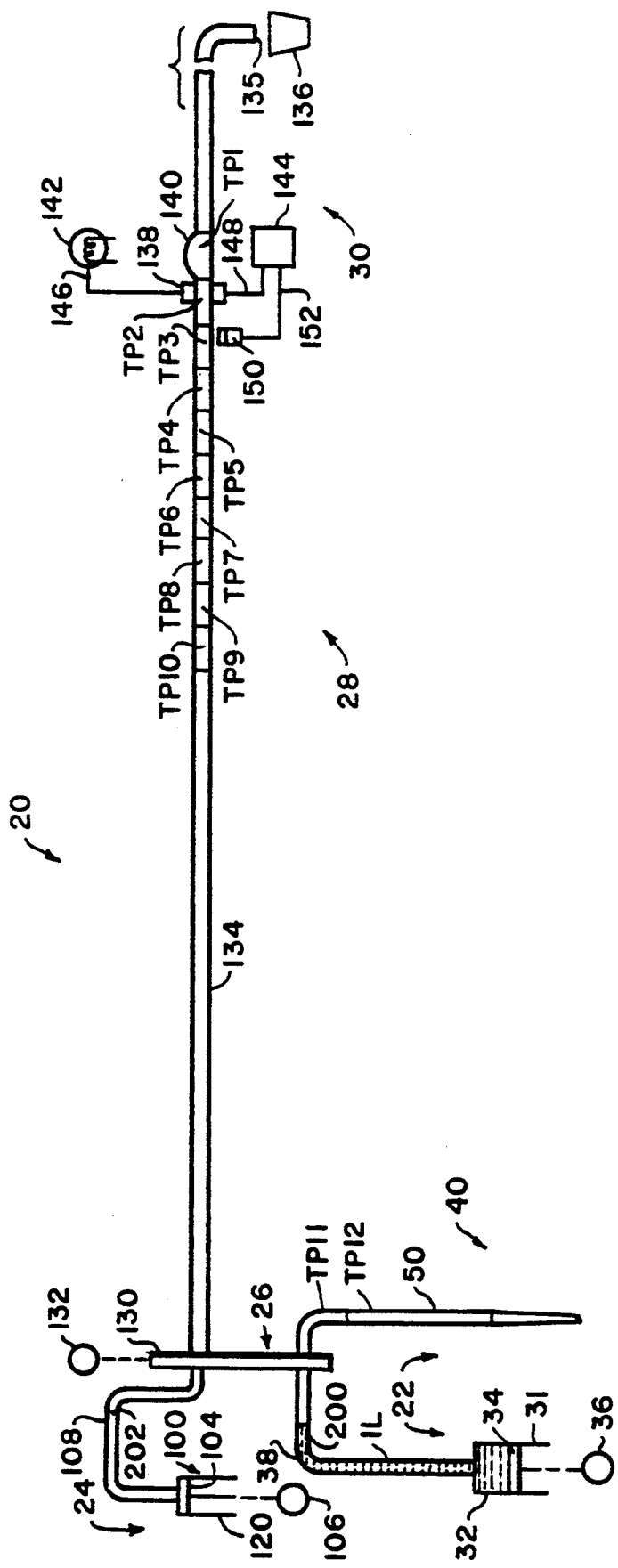

More specifically, and by way of representative example in accordance with the herein disclosed best mode of our invention, for a sample liquid analysis system 20 wherein the displacement of pump 100 is determined by appropriate programming of system controller 153 in accordance with the cross-sectional area of the analytical line 134 to cause air column 202 to bi-directionally displace the test package stream a distance equal to sixteen test package distance in each direction in the analytical line for each complete stroke from bottom dead center of pump 100, and wherein the vanish zone 140 is located a distance along the analytical line from the downstream side of shear valve 130 equal to twenty six test package distances, it will be immediately clear that sample liquid test package TP1 will not reach the vanish zone 140 until ten complete cycles of the system 20 following the introduction of that sample liquid test package to the analytical line. This is illustrated by the somewhat simplified application drawings of FIGS. 14, 15, and 16, respectively: with FIG. 14 illustrating the operational conditions of the system 20 immediately following the introduction of the tenth sample liquid test package TP10 into the analytical line by pump 31, and the shear valve 130 returned to the aspirate position thereof in preparation for the aspiration of sample liquid test package TP12 and resultant displacement of sample liquid test package TP11 from conduit 50 through the shear valve into conduit 38; FIG. 15 illustrating those operational conditions immediately following the displacement by pump 100 of the test package stream sixteen test package positions to the right in the analytical line 134 from the stream position of FIG. 14, thereby causing sample liquid test package TP1 to flow as shown through flow cell 138 into the vanish zone 140, and the displacement of sample liquid test package TP11 from conduit 50 through shear valve 130 into conduit 38 by the formation and aspiration of the succeeding sample liquid test package TP12 into conduit 38 by pump 31 having been partially completed; and FIG. 16 illustrating system operational conditions immediately following the displacement of the test package stream sixteen test package distances to the left in the analytical line 134 by pump 100 to return the same essentially to the starting position thereof at the downstream side of shear valve 130, and the aspiration of sample liquid test package TP12 by pump 31 into conduit 38 having been completed as shown in preparation for the shifting of shear valve 130 into the transfer position thereof and the addition of sample liquid test package TP11 to the test package stream in the analytical line 134 by operation of pump 31 as heretofore described.

For a representative cycle time of thirty seconds for the system 20 of our invention, it will be clear that, in accordance with the above, the residence time of sample liquid test package TP1 for ten system cycles in analytical line 134 prior to the flow as described of the test package through flow cell 138 into the vanish zone 140 will be approximately five minutes; and it will be understood that this resident time is predetermined in accordance with the particular sample liquid analysis chemistries involved to be sufficient to enable the reaction between the included sample and reagent liquids of the test package segment S1+R1 to have proceeded to completion, aided of course by the very thorough mixing of those sample and reagent segment liquids in accordance with repeated test package sloshing in the analytical line as described hereinabove. Thus, and as sample liquid test package TP1 flows for the first time from left to right in the analytical line 134 through flow cell 138 as described with reference to FIG. 13, it will be clear to those skilled in this art that particularly meaningful readings which contribute materially to overall sample liquid analysis accuracy can be taken thereon. More specifically, and for representative sample liquid analysis system applications wherein the sample liquids are human blood samples, and wherein the S1+R1 reaction acts primarily to condition the sample liquid S1 without significant change in sample liquid color, for example sample liquid enzyme activation or modification of sample liquid PH, it will be clear that what is essentially a sample liquid S1 blanking, or pre-incubation insofar as subsequent color-producing reaction with reagent liquid R2 as described hereinbelow, readings may now be taken. In addition, these readings can operate to detect abnormalities in the sample liquid segment S1 in the nature, for example, for human blood sample liquids of broken red cells or clinically significant sample liquid impurities or the like. In like manner, this initial passage of the as yet unmerged reagent liquid segment R2 of the sample liquid test package TP1 through the flow cell 138 as described in the direction from left to right enables accurate baseline or reference readings to be taken thereon to, in combination with the S1+R1 readings, contribute materially to the overall accuracy of the sample liquid analysis results.

Figure 17:
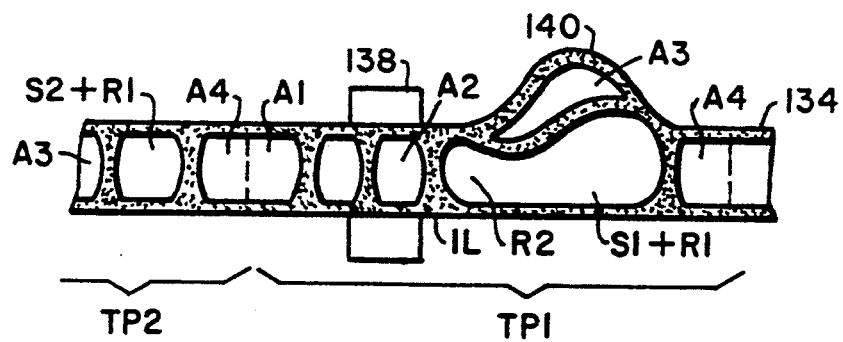
FIG. 17 is an essentially cross-sectional view taken through the sample liquids test package reaction and analysis means of the system of FIG. 1, and illustrates the merger of respective sample and reagent liquid segments therein upon the initial flow of each of the sample liquid test packages therethrough.
Figure 18:
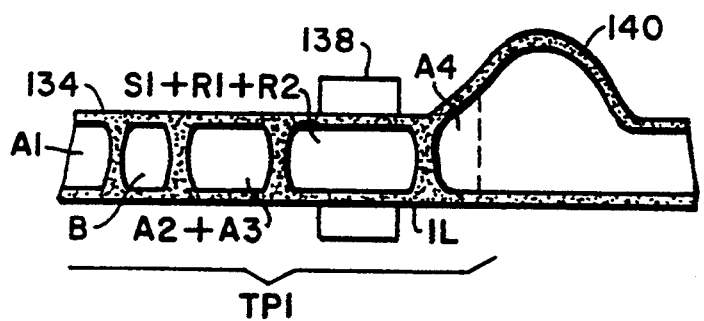
FIG. 18 is a cross-sectional view in the nature of FIG. 17, and illustrates the configuration of a sample liquid test package following flow of same through the sample liquids test package reaction and analysis means as depicted therein.

Since, as described hereinabove, separating air segment A3 of sample liquid test package TP1 is of insufficient volume to occlude the vanish zone 140, it will be clear that this initial flow of that test package into the vanish zone in the direction from left to right as illustrated in drawing FIG. 15 will operate to cause separating air segment A3 to simply float in the respective sample and reagent liquids S1 and R1, and R2, which had formed the S1+R1 and R2 liquid segments resident to either side of the separating air segment A3 prior to the flow of the sample liquid test package TP1 into the vanish zone 140; all to result in the merger of sample liquid test package segments S1+R1 and R2 in the vanish zone 140, and the commencement of the desired color-producing reaction therebetween. This is illustrated by FIGS. 17 and 18 of the application drawings: with FIG. 17 illustrating the flotation as described of the separating air segment A3 of the sample liquid test package TP1 in the vanish zone 140 and the resultant merger therein of the test package segments S1+R1 and R2; and FIG. 18 illustrating the resultant configuration of the sample liquid test package TP1 with those segments merged as described to form a test package segment S1+R1+R2, and separating air segment A3 merged as shown with separating air segment A2, as the test package stream commences its return flow in the analytical line 134 under the action of pump 100 from the vanish zone 140 through the flow cell 138 to the downstream side of shear valve 130, or from the test package stream position of FIG. 15 to the test package position of FIG. 16. The respective volumes of separating air segments A4 and A1, the merged separating air segment A3+A2, and the buffer liquid segment B of the sample liquid test package TP1 are however effective as heretofore described to fully occlude the vanish zone 140, whereby no further change in the configuration of the sample liquid test package TP1, including the leading or trailing separating air segments A4 and A1, as illustrated in FIG. 18 will take place upon this or subsequent passages of the same through the vanish zone. This effectiveness of the vanish zone 140 to cause the merger as described of the sample liquid test package sample and reagent liquids segments S1+R1 and R2 in accordance with the non-occluding volume of the separating air segment A3 is also described in detail in U.S. Pat. No. 4,853,336 as referenced in this specification.

Figure 16:
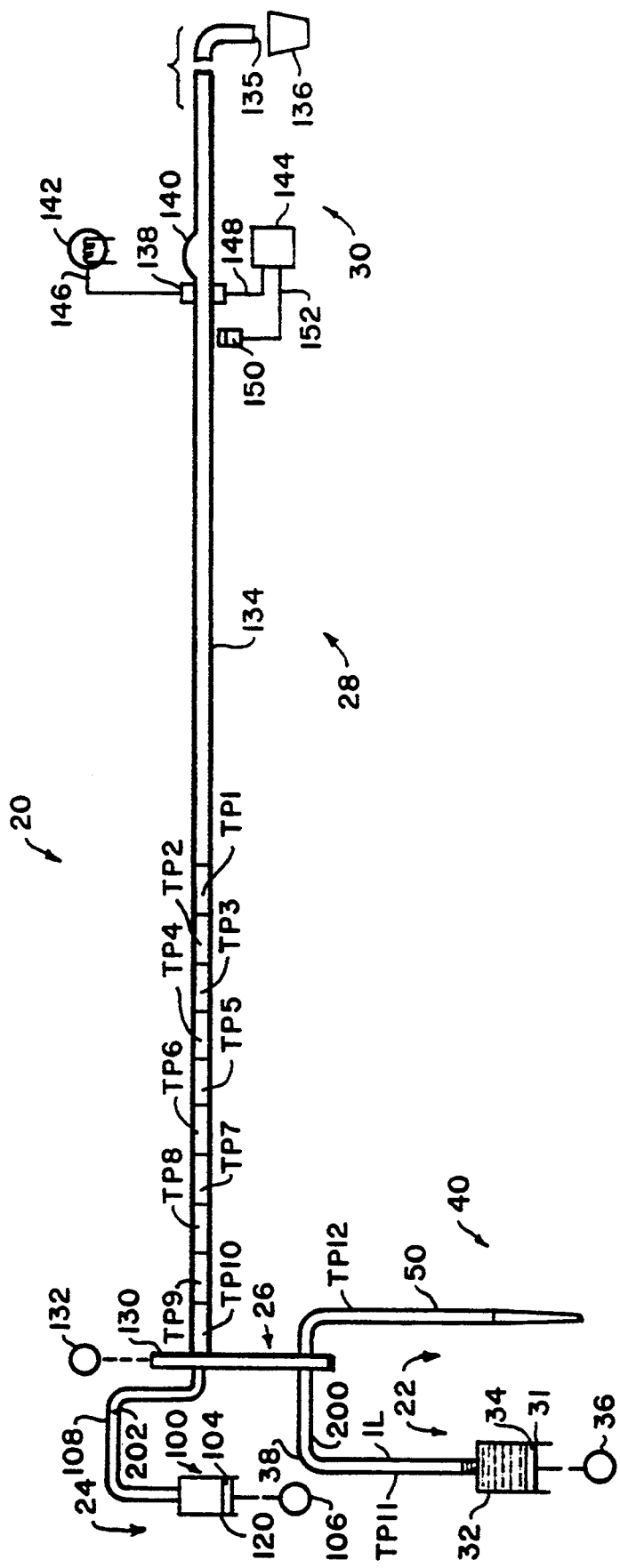

With the system 20 of our invention representatively configured and operable as heretofore described, it will be clear to those skilled in this art that, following the return of the test package stream in the analytical line 134 to the position thereof immediately at the downstream side of shear valve 130 as depicted in FIG. 16, the sample liquid test package TP1, now including the merged and reacting sample and reagent liquid segment S1+R1+R2 as described, will be flowed twice through the flow cell 138 and vanish zone 140, i.e. once in the direction from left to right in the analytical line 134, and once in the direction from right to left therein, for each of the subsequent sixteen cycles of the system 20, or thirty two times in all, before the sample liquid test package TP1 has, as a result of the addition of sixteen subsequent test packages TP11 through TP26 to the test package stream in the analytical line 134 by operation of pump 31 as heretofore described, reached the position in the analytical line immediately to the right of the flow cell 138, inside the vanish zone 140 with piston 104 of pump 100 in the bottom dead center position thereof. The subsequent addition of sample liquid test package TP27 to the test package stream will move test package TP1 to the position immediately to the right of the vanish zone 140; whereupon subsequent bi-directional test package steam displacement in the analytical line by pump 100 as heretofore described will no longer be effective to flow TP1 through either of the flow cell 138 or the vanish zone 140. This operational condition of the system 20 is illustrated by drawing FIG. 19 which makes clear that the test package stream will now include twenty seven sample liquid test packages in the analytical line 134; with test packages TP2 through TP27 residing at or to the left of the vanish zone 140, and test package TP1 residing as shown immediately to the right of the same.

In accordance with a specified thirty second cycle time for the system 20, it will be clear that the specified sixteen system cycles during each of which the sample liquid test package TP1 will pass twice through the flow cell 138 will provide a residence or incubation time of eight minutes for TP1 in the analytical line 134, and during which eight minutes as many as thirty two meaningful readings can be taken by the flow cell 138 on the progress to completion of the S1+R1+R2 reaction, or one per passage of the merged sample and reagent liquids segment S1+R1+R2 through the flow cell. This, of course, provides for highly comprehensive, and thus highly informative and accurate, monitoring of the S1+R1+R2 reaction in terms of the overall sample liquid analysis results through the use of but a single flow cell, and is an additional particularly significant advantage of the sloshing back and forth of the test package stream in the analytical line 134 by the action of pump 100 as heretofore described. Of course, the continued supply as heretofore described of the isolation liquid IL from reservoir 120 by pump 116 to conduit 108, and therefrom through shear valve 130 with the latter in the aspirate position thereof into the analytical line 134 concomitantly with sample liquid test package stream sloshing by air column 202 in accordance with the action of pump 100, insures the replenishment and maintenance of the isolation liquid layer in the analytical line for highly effective sample liquid carry-over minimization.

Figure 19:
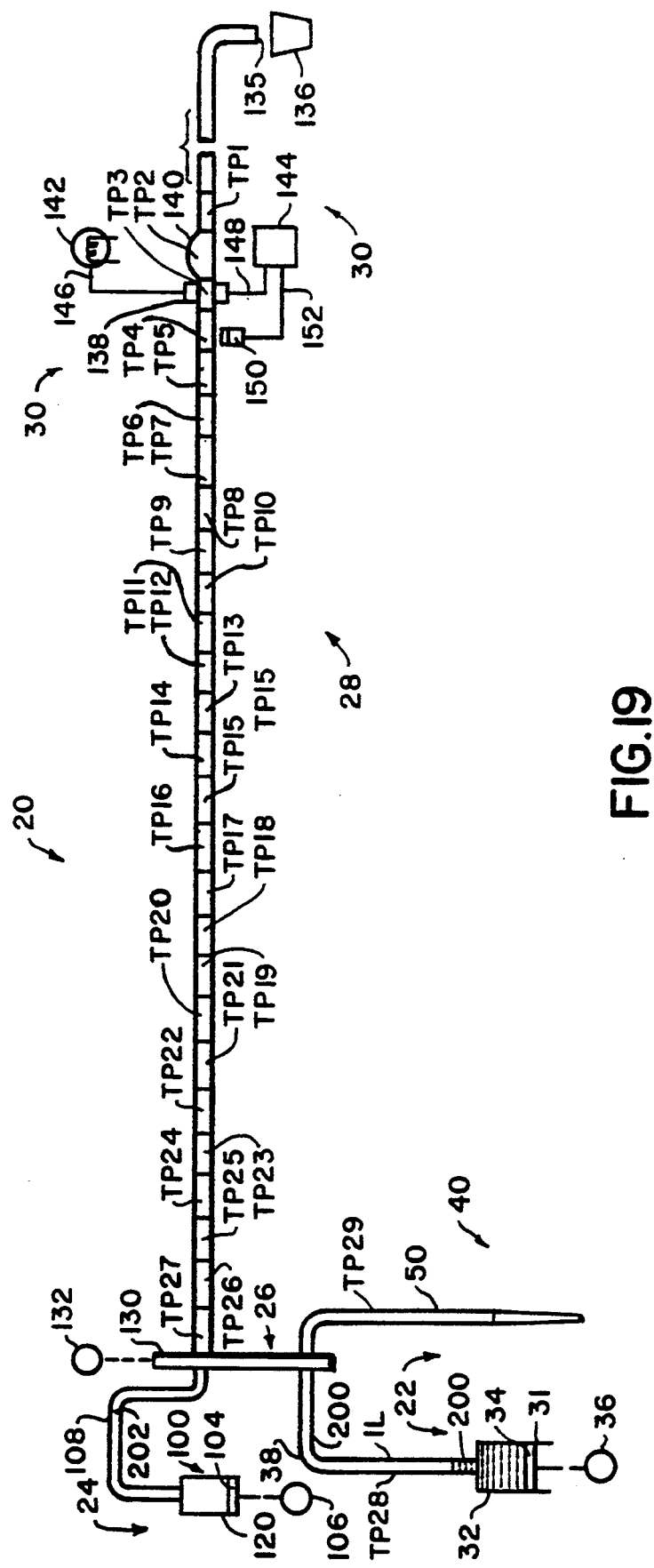
FIG. 19 is a view in the nature of FIGS. 14, 15 and 16 illustrating the operational configurations of the basic system components at a later sequential stage in the reaction and analysis of the sample liquids in the test package stream within the system.

With sample liquid test package TP1 in the position thereof immediately to the right of the vanish zone 140 as depicted in FIG. 19, and with the monitoring of the S1+R1+R2 reaction completed as heretofore described, it will be clear that it is to advantage in terms of overall test package stream length, and resultant stream back-pressure, in the analytical line 134 to dispose of that sample liquid test package to waste upon the next cycle of the system 20, there being nothing further to be gained by the retention of the same therein. To this effect, the length of the analytical line 134 from the downstream side of the vanish zone 140 to the open line end 135 will, in this instance, be made equal to sixteen test package distances, thus providing sufficient analytical line length to the right of the vanish zone to insure retention of TP1 in the analytical line during each of the specified sixteen left-to-right displacements of the test package stream, while nonetheless providing for the flow of TP1 to waste through the open analytical line end upon completion of the next upward stroke of pump piston 104 attendant the next bi-directional test package stream displacement cycle of the system.

Operation of the sample liquid analysis system 20 of our invention constitutes as described; with each of the succeeding sample liquid test packages in the test package stream being retained in turn in the analytical line 134 to the left of the flow cell 138 and vanish zone 140 for ten system cycles for completion of the sample and reagent liquids S+R1 reaction, initially advanced in turn through flow cell 138 into the vanish zone 140 for merger of the respective sample and reagent liquids test package segments S+R1 and R2 and commencement of that reaction, advanced one test package distance and bi-directionally displaced sixteen system cycles to pass through the flow cell 138 and vanish zone 140 thirty two times for readings on the progress to completion of the S+R1+R2 reaction, and flowed in turn to waste through the open end of the analytical line upon the immediately following cycle of the system.

In accordance with the above, it will be immediately clear to those skilled in this art that, with a finite number of discrete sample liquids to be analyzed for a representative run of the sample liquid analysis apparatus 20, for example one hundred, a point will be reached in system operation whereat all of the one hundred sample liquids have been introduced by pump 31 to the analytical line 134, thus leaving no further sample liquids available for the formation of subsequent sample liquid test packages and introduction thereof to the analytical line to advance the test package stream therethrough as required to react and analyze as heretofore described all of the available one hundred sample liquids. At this point in system operation, probe assembly 40 is instructed by appropriate programming of system controller 153 to aspirate only buffer liquid B from container 60, and ambient air, in the formation of subsequent buffer liquid "test" packages—there are, in any event, no further sample liquids available to this effect, and continued aspiration of reagent liquids R1 and R2 would accordingly act to no useful purpose— and these "test" packages are introduced in turn by pump 31 in the manner heretofore described for the sample liquid test packages to the analytical line 134 to continue the advancement as required of the test package stream therein until the reactions and analyses of all of the one hundred available discrete sample liquids have been completed.

Figure 20:
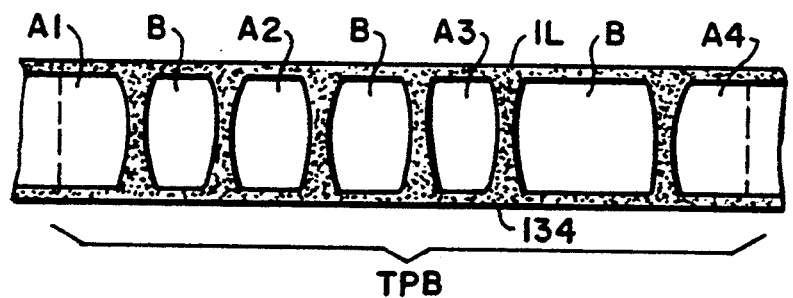
FIG. 20 is an essentially cross-sectional view taken through the sample liquids test package reaction and analysis means of the system of FIG. 1, and illustrates the configuration of a buffer liquid "test" package as is formed and utilized in the system to enable the same to complete sample liquids reaction and analysis on all available sample liquids.
Figure 21:
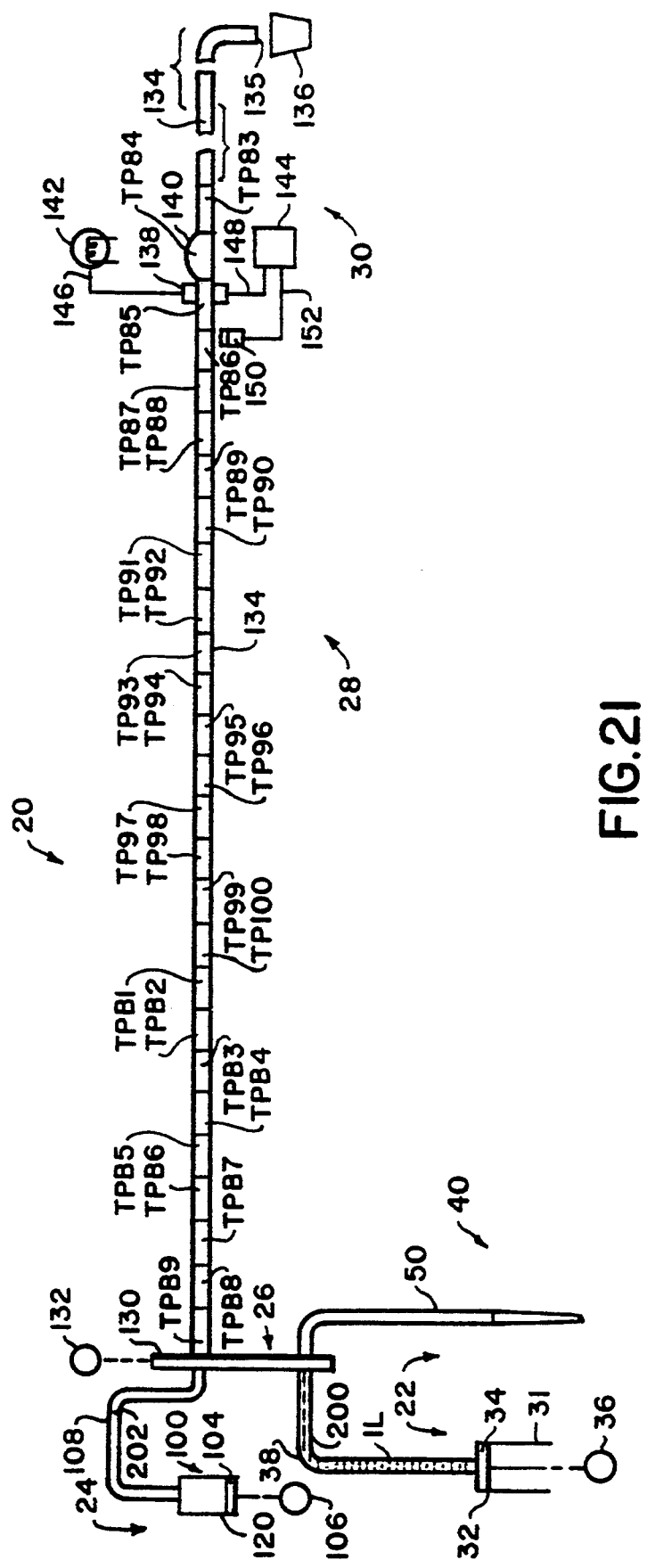
FIG. 21 is a view in the nature of FIGS. 14, 15 and 16 illustrating the operational configurations of the basic system components attendant the use of the buffer liquid "test" packages of FIG. 20 for completion of the sample liquids reactions and analyses on all available sample liquids.

The above is illustrated by drawing FIGS. 20 and 21: with FIG. 20 depicting a buffer liquid "test" package TPB wherein all of the package liquid segments are constituted as indicated by the buffer liquid B aspirated as described by probe assembly 40 from the buffer liquid container 60, but otherwise dimensionally and volumetrically identical to the sample liquid test packages, and substantially encapsulated as shown within the isolation liquid IL from container 88; and FIG. 21 illustrating the operational conditions of the system 20 at the representative point in this sample liquid analysis completion process whereat nine such buffer liquid "test" packages as identified as TPB1 through TPB9 have been introduced in turn by pump 31 through shear valve 130 into the analytical line 134 to advance the last available sample liquid test package TP100 to the tenth position in the test package stream in the analytical line as shown in preparation for the next upward stroke of piston 104 of pump 100 to displace TP100 through flow cell 138 into the vanish zone 140 for the S100+R1+R2 reaction and subsequent repeated sloshing and analysis of TP100 by the system 20 as heretofore described to complete the sample liquid analysis process on all of the available one hundred discrete sample liquids.

If and as required, for example at the commencement of a day's analytical operation of the system 20, the above-described procedure may also be utilized to insure the formation of the sample liquid carryover-minimizing layer of the isolation liquid IL on the interior wall of the analytical line 134 prior to the introduction of the first of the sample liquid test packages thereto, thereby in combination with the ab initio encapsulation of the sample liquid test packages in the isolation liquid IL from reservoir 88 by probe assembly 40, insuring the highest possible degree of sample liquid carryover minimization for all sample liquid analysis operations of the system 20. More specifically, and at system start-up with pump 116 operating to pump isolation liquid IL from reservior 120 into conduit 108, and the isolation liquid column 200 formed in pump cylinder 32 and conduit 38 above piston 34 of pump 31, the probe assembly 40 may be instructed by system controller 153 to initially aspirate only isolation liquid encapsulated buffer liquid "test" packages as illustrated in FIG. 18, and the system repeatedly cycled to introduce these buffer liquid "test" packages to the analytical line 134, repeatedly slosh the same back and forth in the analytical line through the flow cell 138 and vanish zone, and ultimately flow the same through the entire extent of the analytical line to waste through the open end 135 of the line, all as heretofore described, thereby insuring the formation of an effective layer of the isolation liquid IL on the interior wall of the entire extent of the analytical line 134 prior to the introduction of the first sample liquid test package TP1 thereto for the commencement of the actual sample liquid analysis operation.

With further regard to the use as described of the isolation liquid IL for sample liquid carryover minimization purposes, it will be clear that isolation liquid column 200 above piston 34 of pump 31 can be periodically replenished as required by the simple expedient of system controller 153 operating drive motor 76 to temporarily drive rotary valve 72 to the position thereof connecting pump cylinder 32 to the isolation liquid reservoir 70 through conduit 74, and aspiration of the required volume of the isolation liquid into pump cylinder 32 as heretofore described.

Referring now to FIGS. 22, 23, 24, 25 and 26 of the application drawings, a second embodiment of new and improved, reversible direction capsule chemistry sample liquid analysis system, representatively configured and operable in accordance with the currently contemplated best mode of our invention to provide greater throughput in terms of sample liquids analyses per hour than can, as a practical matter, be provided by the system 20 as heretofore described with regard to FIGS. 1–21, with the same sample liquid pre-incubation and incubation times within the system, is indicated generally at 240; and is depicted in the same somewhat simplified schematic form that FIGS. 14, 15 and 19 depict the system 20 of our invention as heretofore described. System 240 is of the same basic configuration, and manner of repeated back and forth sample liquids test package stream sloshing operation through the detecting means, as system 20, and like system components accordingly bear the same reference numerals in FIGS. 22, 23, 24, 25 and 26 as in FIGS. 1–21. In system 240, however, a second detection means as indicated at 242 is provided; and, in the manner of detection means 30 of the system 20, comprises a flow cell as indicated at 244 which is operatively disposed as shown relative to analytical line 134 downstream of flow cell 138 and vanish zone 140. In the manner heretofore described with regard to flow cell 138, flow cell 244 is also of course operable to provide for the colorimetric analyses of sample liquid test packages flowed therethrough; and, to that effect, detection means 242 will be seen to further include light source 246 and bubble detector 248, respectively operatively associated with flow cell 244, analytical line 134, and detector as indicated at 250, by optical fibres 252 and 254, and line 256, respectively. In the manner hereto described for detecting means 30, and although not shown, it will be clear that light source 246, bubble detector 248 and detector 250 of detecting means 242 are also electrically connected to the system controller 153 of FIG. 3 to be operable under the control thereof.

For representative operation of the system 242 with a cycle time of fifteen seconds, rather than thirty seconds as heretofore described with regard to system 20, while nonetheless retaining a residence or pre-incubation time for each of the sample liquid test packages TP in the analytical line 134 of five minutes prior to the initial flow thereof through flow cell 138 into the vanish zone 140, it will be immediately clear to those skilled in this art that each of the test packages will have to be retained in analytical line 134 downstream of flow cell 138 and vanish zone 140 for twenty rather than ten complete cycles of the reversible direction sample liquids test package displacement means 24. Thus, and with system controller 153 again programmed in accordance with the displacement of piston pump 100 and the cross-sectional area of analytical line 134 to operate pump 100 to bi-directionally displace the sample liquids test package stream sixteen test packages in each direction for each complete pump stroke, it will be required that the flow cell 138 and vanish zone 140 be spaced in the analytical line 134 of the system embodiment 240 of FIG. 22 a distance of thirty six rather than twenty six sample liquids test package distances from the downstream side of the linear transfer valve 130. In addition, and again in accordance with the continued sixteen sample liquids test package distances displacement of pump 100, it will be clear that flow cell 244 will be spaced in the analytical line 134 sixteen test package distances downstream from flow cell 138 and vanish zone 140, and that the required length of the analytical line downstream of flow cell 244 to the end 135 thereof will again be equal to sixteen test package distances for the same reasons described in detail hereinabove with regard to the system embodiment 20 of FIGS. 1 through 21.

Figure 22:
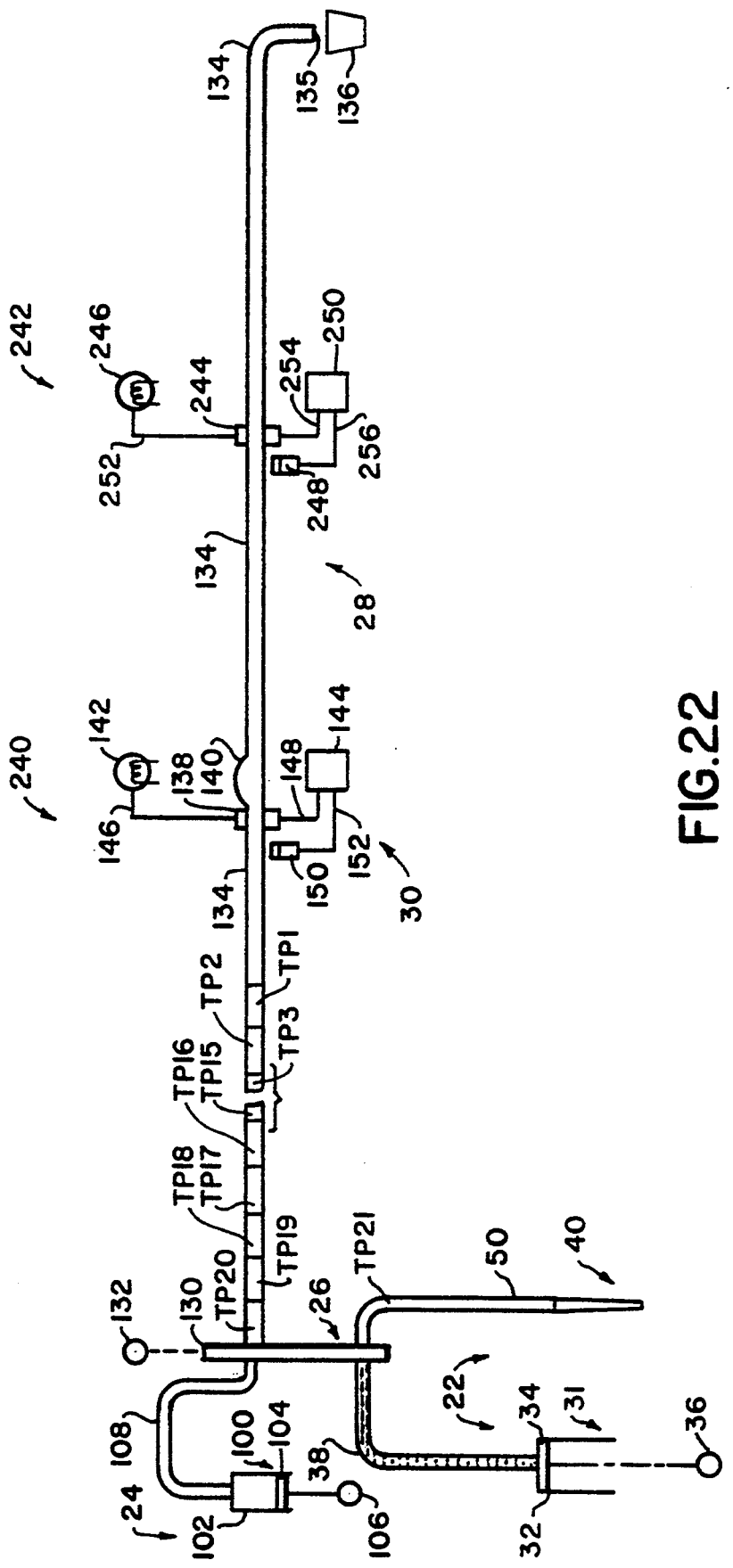
FIGS. 22, 23, 24, 25 and 26 are respectively somewhat simplified schematic diagrams illustrating different operational configurations of a second embodiment of a reversible direction sample liquids analysis system representatively configured and operable in accordance with the currently contemplated best mode of our invention.

FIG. 22 representatively depicts the operational condition of the system embodiment 240 with transfer valve 30 in the aspirate position, wherein the sample liquids test package stream in analytical line 134 is constituted by sample liquids test packages TP1 through TP20, with the succeeding sample liquid test package TP21 having been aspirated as heretofore described through probe assembly 40 and resident in conduit 50, and no sample liquid test package having yet been displaced through flow cell 138 and vanish zone 140.

Figure 23:
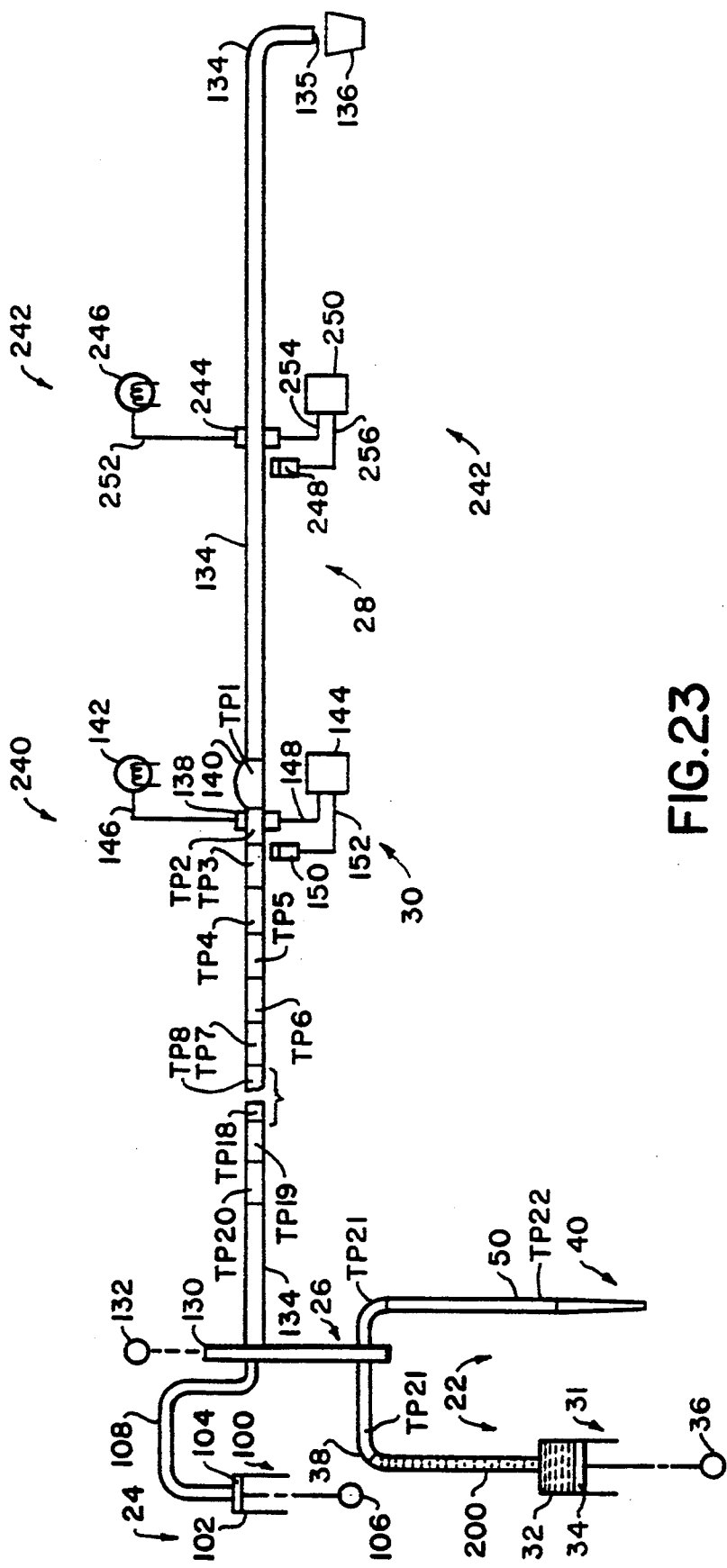

FIG. 23 depicts the operational condition of the system embodiment 240, with the transfer valve 130 in the aspirate position thereof, wherein the sample liquids test package stream TP1 through TP20 of FIG. 22 has been displaced sixteen test packages to the right in the analytical line 134 by the movement of piston 104 of pump 100 from the bottom to top dead center position thereof as shown for initial flow into and through the flow cell 138 and vanish zone 140 of sample liquid test package TP1, with attendant merger as heretofore described of the respective S1, R1 and R2 segments of that sample liquid test package and the commencement of the requisite incubation thereof. Concomitantly, the succeeding sample liquid test package TP21 as aspirated by pump 31 through probe assembly 40 will be resident as shown in conduits 38 and 50 to either side of the transfer valve 130, while the next succeeding sample liquid test package TP22 as aspirated through probe assembly 40 will be resident as shown in conduit 50.

Figure 24:
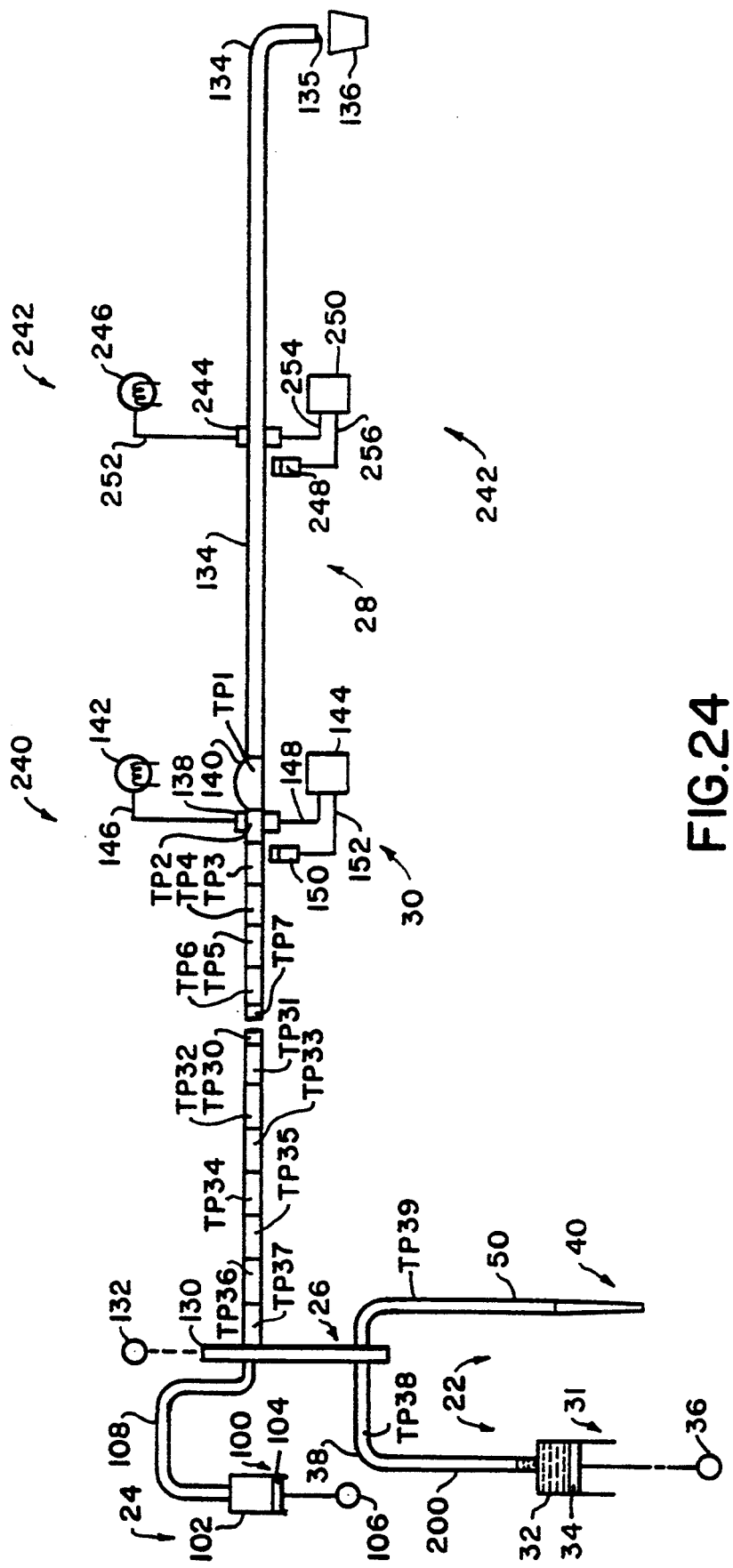

FIG. 24 representatively depicts the operational condition of system embodiment 240 with transfer valve 30 in the aspirate position, wherein the sample liquids test package stream in analytical line 134 is constituted by sample liquids test packages TP1 through TP37, with TP1 having been displaced by downward movement of piston 104 of pump 100 from top to bottom dead center to make its last passage in the downstream direction into and through flow cell 138 and the vanish zone 140 for the next to last reading by flow cell 138 of the S1+R1+R2 reaction on that sample liquid test package. At this point the succeeding sample liquid test package TP38 has been aspirated through probe assembly 40 to reside as shown in conduit 50 and 38 to either side of transfer valve 130; while the next succeeding sample liquid test package TP39 has been aspirated through probe assembly 40 to reside as shown in conduit 50.

Figure 25:
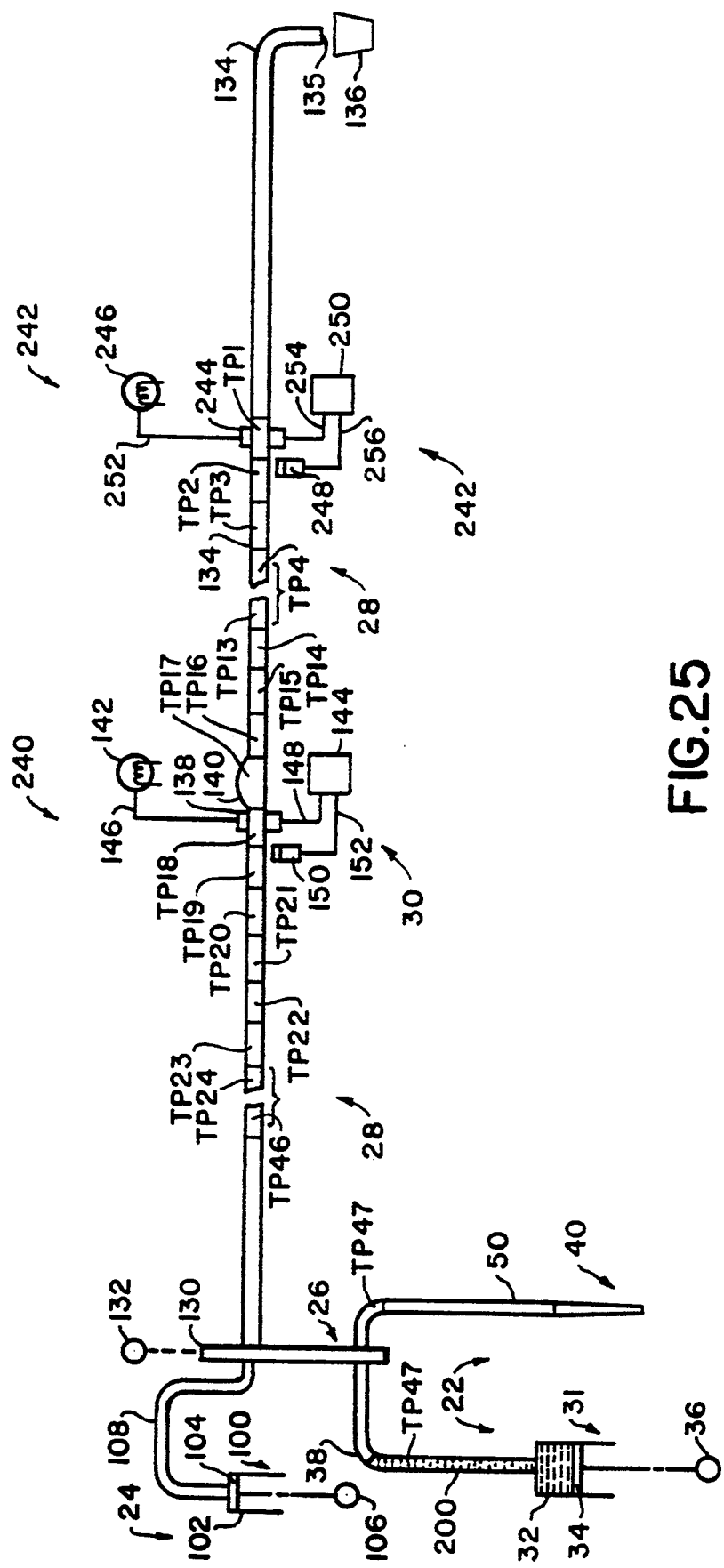

FIG. 25 representatively depicts the operational condition of the system embodiment 240, with the transfer valve in the aspirate position thereof, wherein the sample liquids test package stream in the analytical line 134 is now constituted by sample liquids test packages TP1 through TP46, with test package TP1 having been displaced by upward movement of pump piston 104 of pump 100 to have made its first passage in the downstream direction into flow cell 244 for the commencement of colorimetric readings thereon by that flow cell; the succeeding sample liquid test package TP47 having been aspirated by pump 31 through probe assembly 40 to reside as shown in conduits 38 and 50 to either side of the transfer valve 130; and the next succeeding sample liquid test package TP48 having been partially aspirated through probe assembly 40 to reside as shown in conduit 50.

Figure 26:
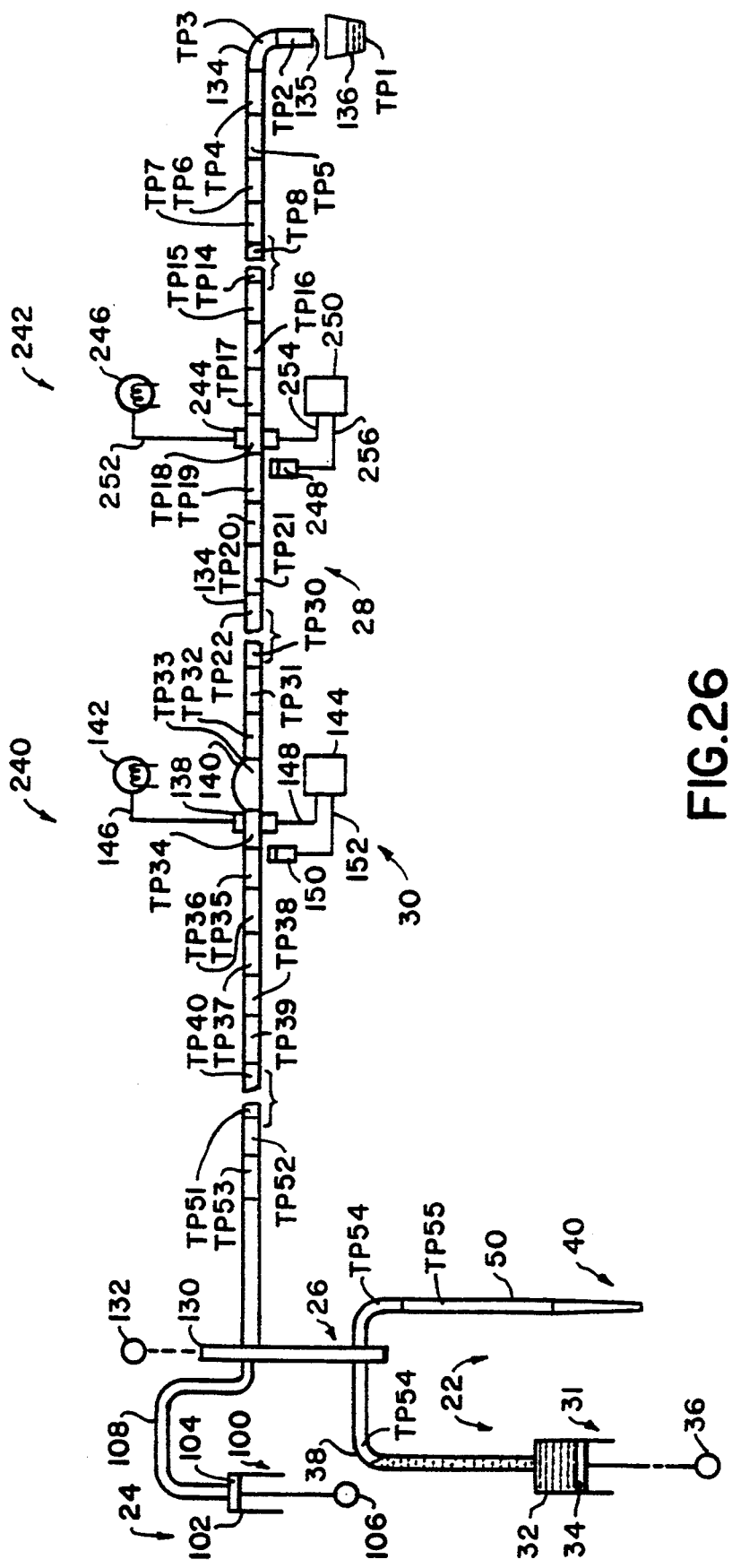

FIG. 26 representatively depicts the system embodiment 240 in the operational condition thereof, again with the transfer valve 130 in the aspirate position, wherein the sample liquids test package stream in the analytical line is constituted by sample liquids test packages TP2 through TP53, with sample liquid test package TP1 having been displaced by the movement of pump piston 104 of pump 100 from bottom to top dead center to have flowed as shown from the open end 135 of the analytical line 134 into waste container 136 having completed its requisite number of flow cycles through that analytical line.

Final operation of the system 240 to, for example, complete a run as described on a series of two hundred and forty discrete sample liquids test packages is accomplished in the same manner as that described hereinabove in conjunction with FIGS. 20 and 21 regarding system embodiment 20; and will thus be immediately understood to comprise the aspiration, formation and bi-directional displacement through the system embodiment 240 of the air and buffer liquid, only, packages TPB as depicted in FIG. 20 until the sample liquid test package TP240 has completed its bi-directional transit as described of the analytical line 134 and been discharged therefrom into waste container 136.

Under the above circumstances, it will be clear to those skilled in this art that each of the duly incubated sample liquid test packages will have been "read" sixteen times for fifteen seconds at each of the flow cells 138 and 244, for a total of four minutes "reading" time at each of the same, and a total "reading time" of eight minutes with fifteen second intervals therebetween. This provides for a total of thirty two, time-spaced readings on each of the sample liquid test packages through the use of only two flow cells; and highly comprehensive and accurate sample liquid-reagent liquids reaction analysis results as described in detail hereinabove. With a representative cycle time as described of fifteen seconds for the system embodiment 240 of FIGS. 22 through 26, it will also be clear that a throughput of two hundred and forty sample liquids test packages per hour can be provided by the same once steady-state system operational conditions have been reached.

Figure 27:
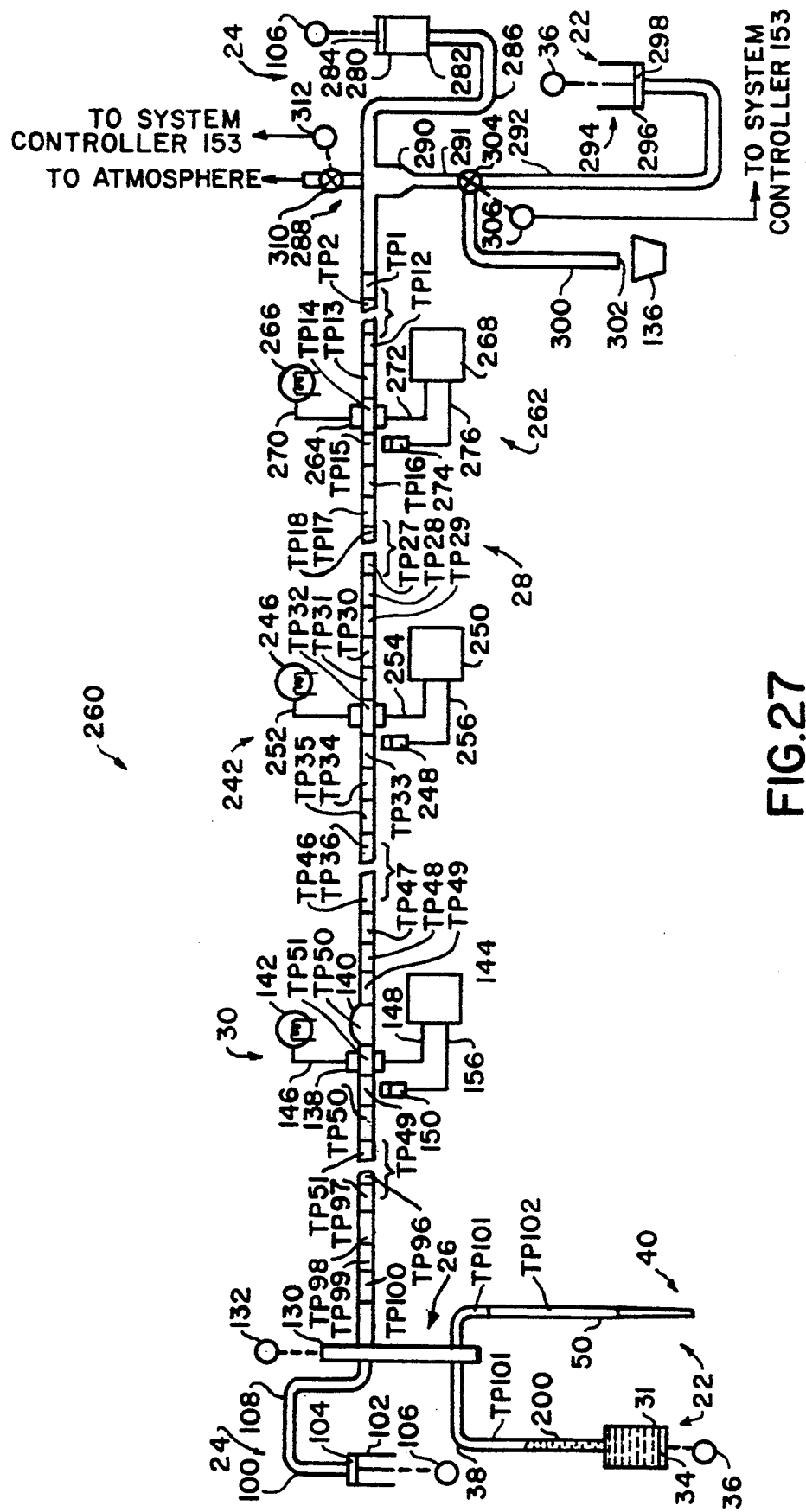
FIGS. 27 and 29 are respectively somewhat simplified schematic diagrams illustrating different operational configurations of a third embodiment of the reversible direction sample liquids analysis system representatively configured and operable in accordance with the currently contemplated best mode of our invention.
Figure 28:
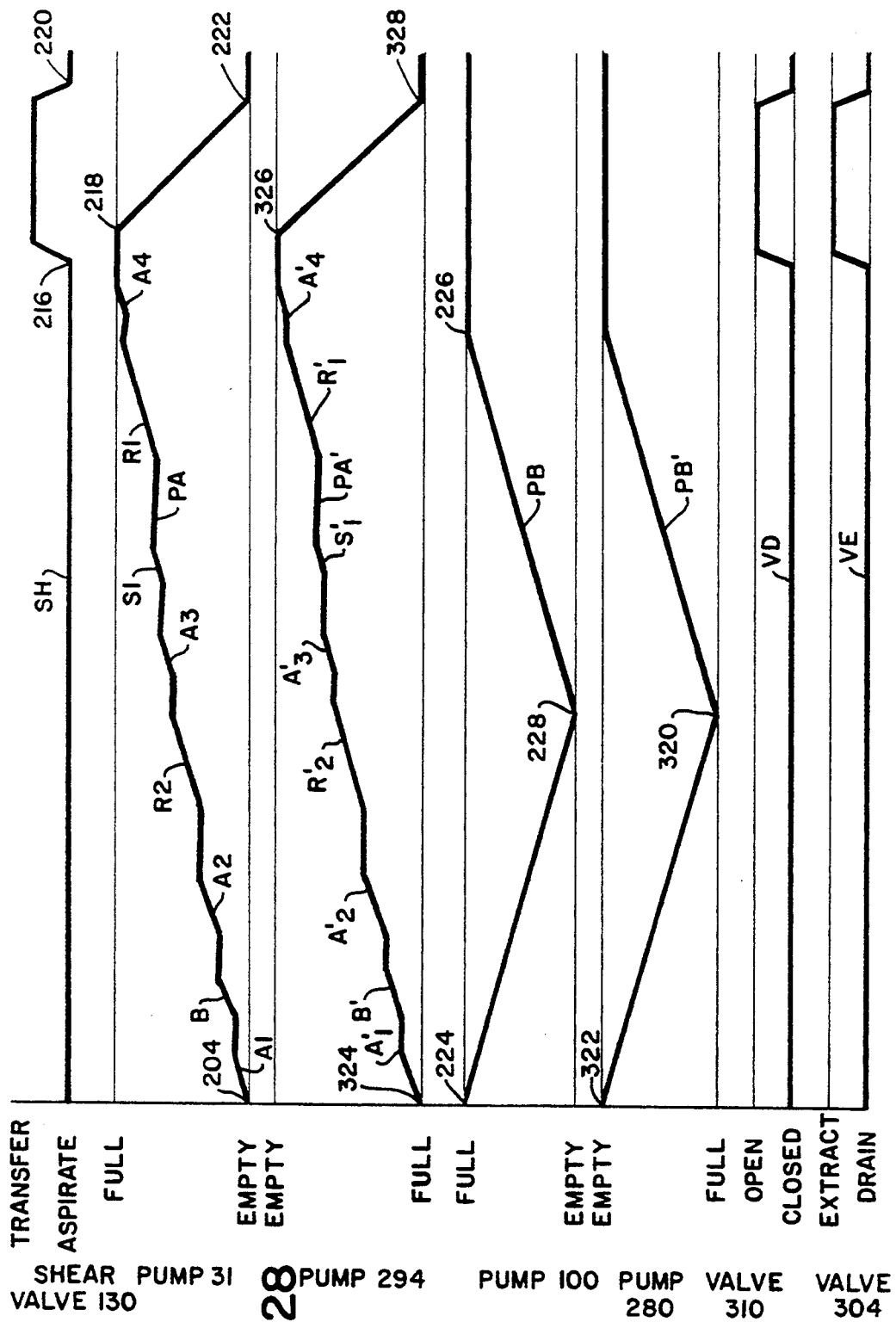
FIG. 28 is a timing diagram illustrating the operations of the front and back system end positive displacement pumps and the shear and sample liquid test package extraction control valves of the system of FIGS. 27 and 29.
Figure 29:
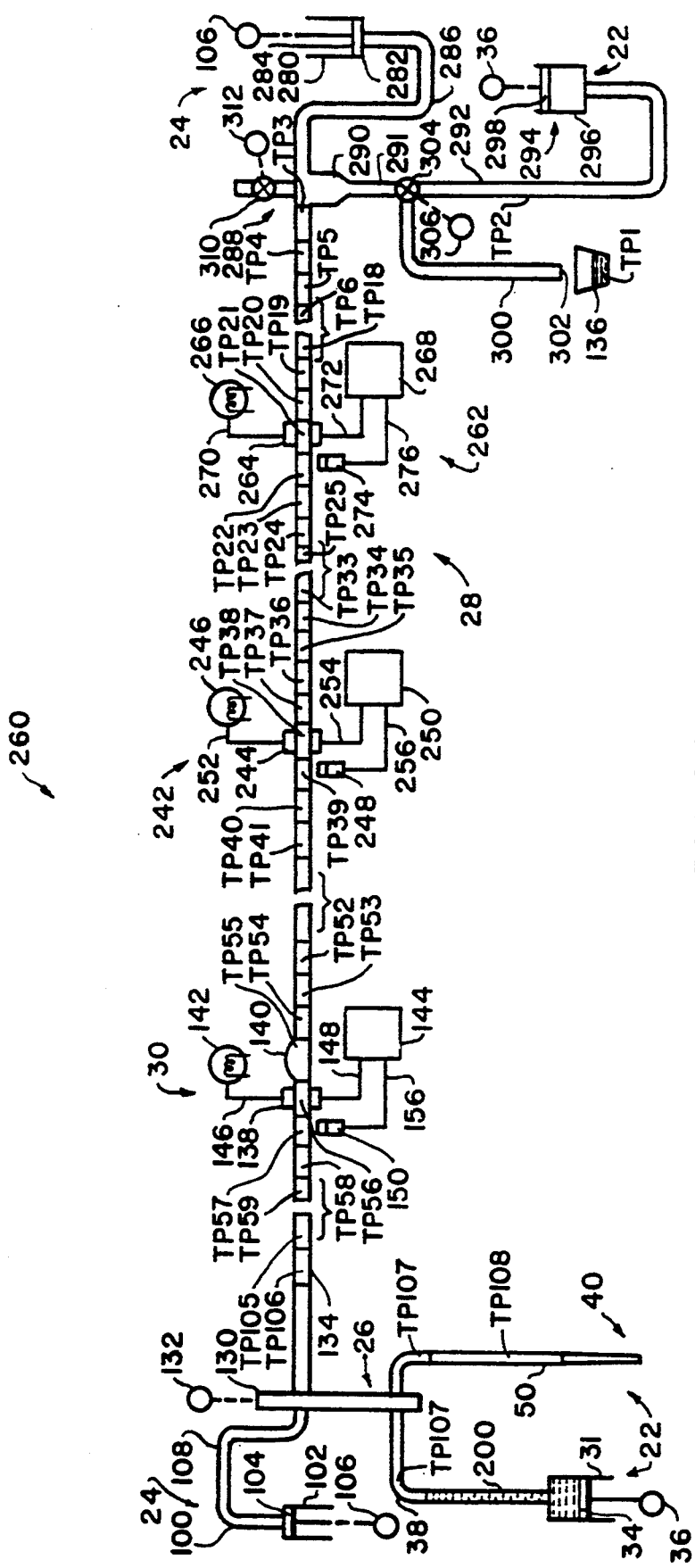

Referring now to FIGS. 27 through 29, a third embodiment of new and improved, reversible direction capsule chemistry sample liquid analysis system, representatively configured and operable in accordance with the currently contemplated best mode of our invention is indicated generally at 260; and is operable to provide even greater throughput in terms of sample liquids analyses per hour than can, as a practical matter be provided by the system embodiment 20 of FIGS. 1 through 22, or the system embodiment 240 of FIGS. 22 through 26, with the same five minute sample liquid test package pre-incubation time for the S+R1 segments of each of the sample liquid test packages, and virtually the same eight minute incubation time for the S+R1+R2 segments of each of those sample liquid test packages.

System embodiment 260 is again of basically the same configuration, and means of repeated back and forth sample liquids test package stream sloshing operation through the detecting means, as the system embodiments 20 and 240; and like system components accordingly again bear the same reference numerals in FIGS. 27, 28 and 29, as in FIGS. 1 through 21, and FIGS. 22 through 26, respectively. In system 260, however, a third detection means as indicated generally at 262 is provided as shown in the analytical line 134 downstream of the second detection means 242; and, in the manner of the latter, comprises a flow cell 264, a light source 266, a detector 268 with optical fibres 270 and 272 conveying light from the source 266 through the flow cell 264 to detector 268 in conventional, colorimetric manner. In addition, another bubble detector as indicated at 274 is operatively associated as shown with the analytical line 134 immediately upstream of flow cell 264 and operatively connected to the latter as indicated by line 276. In the manner of detecting means 30 and 242, and although not shown, it will be clear that the light source 266, the bubble detector 274 and the detector 268 of the detecting means 262 are also electrically connected to the system controller 153 of FIG. 3 to be operable under the control thereof.

For representative operation of the system embodiment 260, a cycle time of nine seconds, and a displacement of pump 100 equal to eighteen rather than sixteen sample liquids test package distances, are programmed into system controller 153 of FIG. 3 to control system operation. In accordance with those operational parameters, and in order to continue to provide for the same five minute pre-incubation time, and essentially the same eight minute incubation time, for each of the sample liquid test packages, it will be understood that flow cell 138 will have to be spaced in analytical line 134 thirty three plus eighteen, for a total of fifty one, sample liquids test package distances from the downstream face of transfer valve 130; that flow cell 244 will have to be spaced in analytical line 134 eighteen sample liquids test package distances downstream of flow cell 138; that flow cell 264 will be spaced in analytical line 134 a distance of eighteen sample liquid test packages downstream of flow cell 242; and that a further effective extent of analytical line 134 of eighteen sample liquid test package distances will have to be provided downstream of flow cell 264. This results in a total effective length for the analytical line 134 of one hundred and five sample liquid test package distances; and, in accordance with the practical fluidic requirements regarding the requisite particularly precise positive pumping of the sample liquids test package stream inherent in the operation of the system of our invention, has been determined to require positive displacement sample liquids test package stream pumping at both the "front" and "back" ends of the system embodiment 260.

More specifically, and as clearly illustrated in FIG. 27, this requirement is met in particularly effective manner in the system 260 by the provision of an additional positive displacement pump, again preferably taking the form of a precisely operable syringe pump of readily adjustable stroke, as indicated generally at 280, and comprising cylinder 282 and pump piston 284; and operatively connected as shown by a connecting conduit 286 to what is the effective terminus of analytical line 134 as indicated generally at 288. As indicated, the piston 284 of pump 280 is also driven by the same drive motor 106 that drives the piston 104 of pump 100; and it will be understood that pump pistons 104 and 284 are mechanically coupled to drive motor 106 in such manner so that when one of same is moving from bottom to top center, the other is moving from top to bottom dead center, and vice versa, and that when one of those pump pistons is at top dead center, the other is at bottom dead center, and vice versa. Thus, pumps 100 and 280 will be understood to be operable in "push-pull" manner with regard to the sample liquids test packages stream in analytical line 134 to effect particularly precise differential pumping with regard to the same; with the concomitant exhaust stroke of pump 100 and intake stroke of pump 280 functioning to precisely advance the sample liquids test package stream in the analytical line 134 eighteen sample liquids test packages distances the right as seen in FIG. 27, and the concomitant intake stroke of pump 100 and exhaust stroke of pump 280 functioning to retract that stream in the analytical line that same number of test package distances in the direction to the left as seen in FIG. 27. Under these circumstances, it will be clear that particularly precise reversible direction flow of the sample liquids test package stream in the analytical line 134 as described in detail hereinabove with regard to system embodiments 20 and 260 is retained in the system embodiment 260 despite the lengthening of the analytical line 134, and the addition of the third flow cell 264 thereto.

Since the analytical line 134 no longer terminates in an open end in the system embodiment 260, it will be clear that other means will have to be employed therein for the precise extraction in turn of each of the sample liquid test packages upon the completion thereby of the requisite number of cycles through the system. To this effect, a funnel-like conduit portion as indicated at 290, and of volume sufficient to prevent the occlusion thereof by a sample liquid test package, is provided as shown to in essence bridge the connection between the effective terminus 288 of the analytical line 134 and the conduit 286 and extend downwardly therefrom to neck down into a conduit 291.

A three way rotary valve is indicated at 304, and is driven as shown by an electric drive motor 306 under the control of system controller 153; and conduit 291 is connectable therethrough to another positive displacement pump, again preferably taking the form of a precisely operable syringe pump of readily adjustable stroke, as indicated generally at 294, and comprising a cylinder 296 and a piston 298, as indicated, the piston 298 of pump 294 is also driven by the same drive motor 36 that drives the piston 34 of pump 31; and it will again be understood that pump pistons 34 and 298 are mechanically coupled to drive motor 36 in such manner so that when one of the same is moving from top dead center to bottom dead center, the other is moving from bottom dead center to top dead center, and vice versa, and that when one of the same is at top dead center the other is at bottom dead center, and vice versa. Thus, and in the manner heretofore described with regard to pumps 100 and 280, pumps 31 and 294 will also be understood to be operable in "push-pull" fashion to effect particularly precise differential pumping with regard to the concomitant injection and extraction of the sample liquids test packages into and from the sample liquids test package stream in analytical line 134.

A drain conduit is indicated at 300, and terminates as shown in an open end 302 directly above waste container 136. The other end of the drain conduit 300 connects as shown to three way rotary valve 304 which, in a first valve position, permits fluid flow between conduits 291 and 292 and closes off drain conduit 300; and, in a second valve position connects conduit 292 to the drain conduit 300 thereby closing off fluid flow communication between conduits 292 and 291.

A conduit 308 extends as shown to atmosphere from the juncture of analytical line 134 and conduit 286 directly above the funnel-like conduit portion 290; and two-way rotary valve 310 is operatively disposed in conduit 308 and driven by electric drive motor 312 as indicated under the control of system controller 153 between open and closed valve positions.

FIG. 28 is a timing diagram illustrating the respective operational conditions of shear valve 130, pumps 31, 294, 100 and 280, and rotary valves 310 and 304 of the system embodiment 260 of FIG. 27 during a representative operational cycle of that system embodiment. To that effect, line SH illustrates the respective aspirate and transfer conditions of shear valve 130; line PA illustrates the position of piston 34 in cylinder 32 of pump 31 attendant the aspiration, formation and insertion into analytical line 134 of a sample liquid test package; line PB illustrates the position of piston 104 in cylinder 102 of pump 100 attendant the bi-directional displacement of the sample liquids stream as described in analytical line 134 eighteen test package distances in the downstream and then upstream directions, respectively; line PA' illustrates the position of piston 298 in cylinder 296 of pump 294 attendant the "push-pull" operation of that pump with the coupled pump 31 to clearly depict the concomitance of the insertion of a sample liquid test package into the analytical line by pump 31, and the pumping to waste by pump 294 as described in detail hereinbelow of the sample liquid test package which is then in the funnel-like conduit portion 290 at the terminus of analytical line 134 one hundred and five sample liquid test packages ahead of the newly inserted sample liquid test package; line PB' illustrates the position of piston 284 in cylinder 282 of pump 280 attendant the "push-pull" operation of that pump with the coupled pump 100 to clearly depict the concomitance of the operation of those pumps as described in detail hereinbelow with regard to the bi-directional displacement of the sample liquid test package stream in the analytical line eighteen test package distances in each direction; line VD illustrates the operational conditions of the two way rotary valve 310; and line VE illustrates the operational conditions of the three way rotary valve 304; it being immediately clear to those skilled in this art that all lines in the timing diagram of FIG. 28 are drawn to the same time scale.

In FIG. 28 points 216 and 220 on line SH, points 204, 218 and 222 on line PA, and points 224, 228 and 226 on line PB indicate the same points in time in an operational cycle of the system embodiment 260 of FIG. 27 as illustrated by those like-numbered points on the timing diagram of FIG. 4 for the system embodiment 20 of FIGS. 1 through 21. In addition point 320 on line PB' in FIG. 28, which is time-coincident with point 228 on line PB makes clear that the piston 104 of pump 100 is at the top dead center when the piston 284 of pump 280 is at bottom dead center; while point 322 on line PB' which is time-coincident with point 224 on line PB makes clear that the exact opposite is also true with regard to the coupled pumps 100 and 280. Likewise for points 324 and 326 and 328 on line PA' which are respectively time-coincident with points 204, 218 and 222 on line PA, and make clear that this exact same relationship is also true with regard to the position of piston 34 in cylinder 32 of pump 31 vis-a-vis the position of piston 298 in cylinder 296 of pump 294.

With the exception of the operation of the coupled, position displacement pumps 280 and 294, and valves 304 and 310, as described in detail directly hereinbelow, operation of the system embodiment 260 may be understood to be essentially the same as the operations of system embodiments 20 and 260 as described in detail hereinabove; with the sample liquid test package stream being formed as described and inserted into the analytical line 134 by the operations of probe assembly 40 and, in this instance by the "push-pull" actions of the coupled pumps 31 and 294; bi-directionally displaced in the analytical line 134 to flow repeatedly through each of the flow cells 138, 244 and 264 in both directions, following merger of the respective S1 and R1 and R2 segments of each of the sample liquid test packages upon the initial flow of the same into the vanish zone 140, in this instance by coupled pumps 100 and 280; and ultimately discharged seriatim from the analytical line 134 to the waste container 136, in this instance also by the "push-pull" actions of the coupled pumps 31 and 294.

More specifically, and referring again to FIG. 27 which depicts the transfer valve 130 of system embodiment 270 in the aspirate position, it will immediately be seen that the displacement of the sample liquids test package stream, there consisting of sample liquids test packages TP1 through TP100, eighteen sample liquids test package distances to the right in the analytical line 134 will have been accomplished in "push-pull" fashion by the concomitant movement of the piston 104 of pump 100 from the bottom to top dead center positions thereof, and of the piston 284 of pump 280 from the top to bottom dead center positions thereof. At this point in the operation of system 260, rotary valve 310 is closed, while rotary valve 304 connects conduit 292 to drain conduit 300, thereby enabling the movement of piston 298 of pump 294 from bottom dead center to top dead center to simply pump air out through the drain conduit, and sealing off the analytical line 134 to insure the precision of the differential pumping action of the coupled pumps 102 and 280 in bi-directionally displacing the sample liquids test package stream. At this point in time, succeeding sample liquid test packages TP101 and TP102 have been aspirated as heretofore described by pump 31 through probe assembly 40 to respectively reside as shown in conduits 38 and 50.

FIG. 29 depicts the system embodiment 260 with the transfer valve 130 in the transfer position thereof, and illustrates the sample liquid test package TP106 having just been inserted by the movement of piston 34 of pump 31 from the bottom to top dead center positions thereof through the transfer valve 130 into the sample liquids test package stream in the analytical line to advance that stream one test package distance to the right as heretofore described. This results in the sample liquid test package TP2 which has now completed its bi-directional journey through analytical line 134 falling into funnel-like conduit portion 290; and, with rotary valve 304 switched to now connect conduits 291 and 292, now being drawn by the concomitant movement of piston 298 of pump 294 from top to bottom dead center from conduit 291 through the valve into conduit 292. As this occurs, rotary valve 310 is switched to the open position thereof to allow atmospheric pressure to enter the system therethrough to balance the pressure inside analytical line 134. Thus, precise insertion of the sample liquid test package TP106 into the analytical line 134, and concomitant precise extraction of the sample liquid test package TP2 therefrom are insured by the positive displacement, differential pumping action of the coupled pumps 31 and 294.

In accordance with the above, it will be understood by those skilled in this art that, immediately upon the return of the transfer valve 130 to the aspirate position thereof, and the movement of piston 34 of pump 31 from the top to bottom dead center positions thereof to aspirate the next succeeding sample liquid test package TP108 (not shown) into conduit 50 through probe assembly 40, valve 310 will be switched to the closed position thereof, and valve 304 switched to the position to connect conduits 292 and drain conduit 300; whereupon the concomitant movement of the piston 298 of pump 294 from the bottom to top dead center positions thereof will be effective to pump sample liquid test package TP2 from conduit 292 through valve 304 into drain conduit 300 and through the open end 302 of the latter into waste container 136 to join sample liquid test package TP1 as already resident therein.

In accordance with the nine second cycle time, and the other relevant operational parameters of the system embodiment 260, it will be clear that each of the sample liquid test packages will be "read" eighteen times for a total of 2.7 minutes at each of the flow cells 138, 244 and 264, for a total sample liquid "reading" time of 8.1 minutes. This provides for a total of fifty four time-spaced readings on each of the sample liquid test packages through the use of only three flow cells, and resultant highly accurate and comprehensive sample liquids-reagent liquids reaction analysis results as described in detail hereinabove. Also, and in accordance with the representative nine second cycle time as described for the system embodiment 260, it will be clear that a sample liquids test package throughput of fully four hundred sample liquids test packages can be readily provided thereby once steady-state system operational conditions have been met.

Completion of the flow through the system embodiment 260 of any plurality of sample liquid test packages, for example a run of four hundred of the same, is again completed as described in detail hereinabove with regard to application drawing FIG. 20 through use of the air and buffer liquid "test" packages only following the insertion of TP400 into the analytical line by pump 31. Of course, and in addition to completing the flow of all of the sample liquids test packages of a particular run through all of the hereindisclosed embodiments of the system of our invention, this utilization of air and buffer liquid, only, "test" packages for run completion also functions to very thoroughly cleanse the relevant system components of any possible remaining sample liquids residue in preparation for the next system run, thereby even further minimizing sample liquids carry-overs.

By all of the above is believed made clear that our invention provides sample liquid analysis system and method which, although suitable for application to a wide variety of analyses on a wide variety of sample liquids, are particularly adapted to the automated clinical analyses in turn of human bioligical sample liquids. These sample liquids would include human blood sera, human blood plasma, urine and cerebral spinal fluid; and the clinical analyses would include homogeneous blood chemistry assay, for example immunoassays or enzyme assays, wherein a significant plurality of precisely timed analyses on the course to completion of the $S+R1+R2$ reaction for each of the sample liquids in turn are required by the applicable chemistries and, in the case of enzymes, also applicable international guidelines, for the provision of meaningful overall sample liquids analysis results.

Although depicted and described herein as of essentially straight configuration, it will be clear that the analytical line 134 could alternatively be of generally circular configuration without adverse effect on the operation of the system 20 to thus reduce system space requirements.

Figure 30:
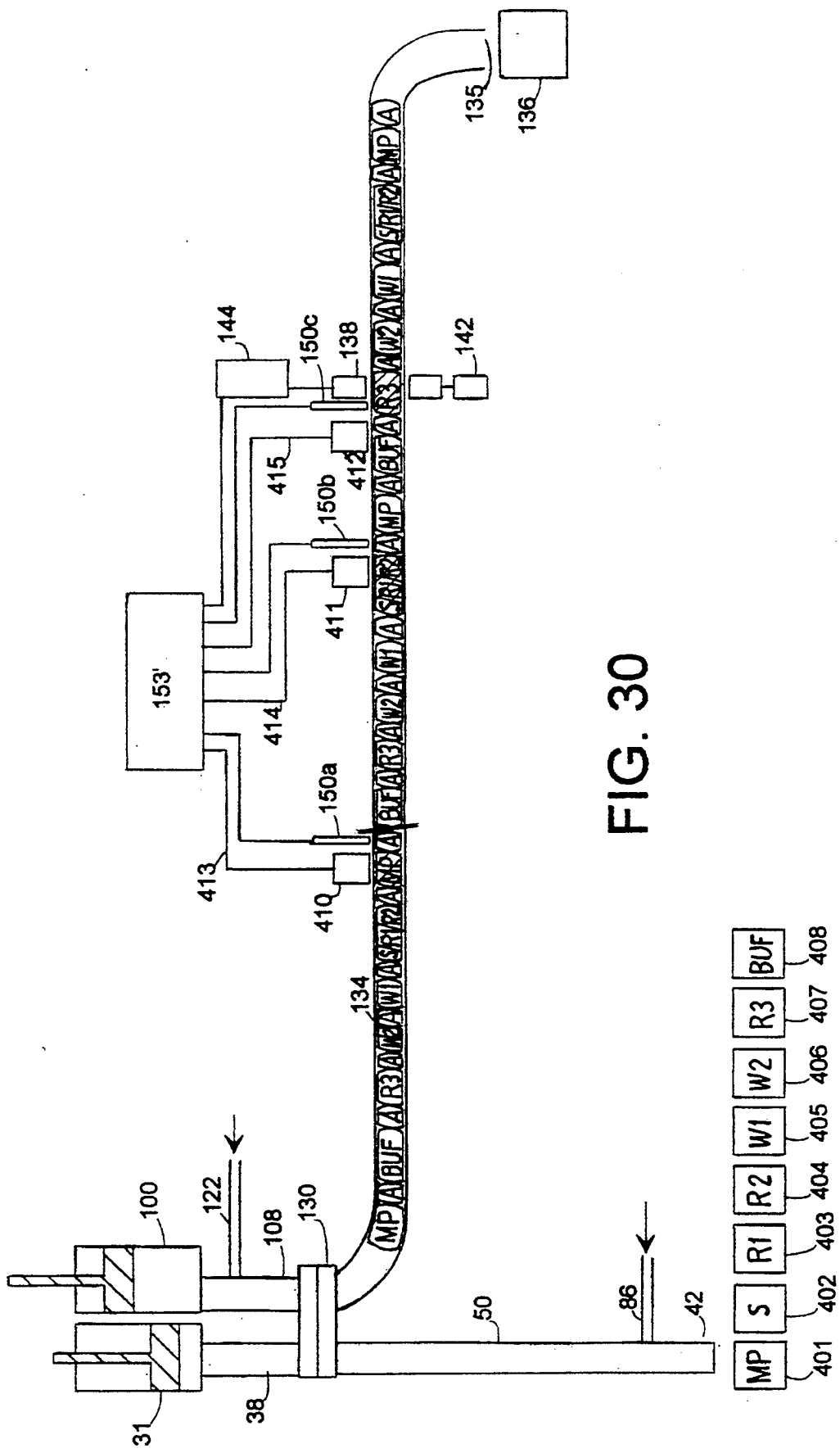
FIG. 30 is a schematic diagram of an embodiment of the present invention for use in an immunoassay.

Referring now to FIG. 30, the elements used for effecting an immunoassay which are common to the reversible direction capsule chemistry sample liquid analysis system and method, described with regard to FIGS. 1-29, are portrayed with the same reference numbers.

A continuous series of test capsules for a magnetic particle-based heterogeneous immunoassay is shown in FIG. 30. Each test capsule consists of aliquots of a sample, magnetic particles, reagents required for the assay and the needed number of wash segments. The magnetic particles are contained in suspension in container 401, the sample is in container 402, reagent R1 is in container 403, reagent R2 is in container 404, the first washing liquid W1 is in container 405, the second washing liquid W2 is in container 406, the reagent R3 is in container 407 and a buffer solution is in container 408.

In a preferred embodiment 7 microliters of the sample, 10.5 microliters of reagent R1 and 10.5 microliters of reagent R2 are aspirated from separate containers and are caused to merge into a single liquid capsule in probe 42 or in the analytical line 134.

Approximately 30 microliters of each remaining substance is aspirated by probe 42 into tube 50 and thereafter transferred to tube 134 via the shear valve 130 in the manner described hereinabove.

As in those previously described embodiments, the segments of each liquid and each separating air bubble is encapsulated by an isolating liquid which completely surrounds them and prevents contact of the segments with the inner surface of tube 134. Each liquid segment is preferably separated by an air segment which further prevents the undesired mixing of the segments.

By means of a system of magnets 410–412 which are connected via wires 413–415 to system controller 153' and bubble detectors 150a–150c connected to controller 153', the magnetic particle-based immunoassay can be carried out without any additional hardware. The bubble detectors 150a–c are preferably those which can detect a liquid/gas interface travelling in either longitudinal direction. A bubble detector of that type is disclosed in copending U.S. application Ser. No. 08/106,255, filed Aug. 13, 1993 and assigned to the same assignee, the disclosure of which is hereby incorporated by reference.

In a typical immunoassay, the sample S is allowed to react with reagents R1 and R2 in a liquid segment within the test capsule for a fixed period of time, as defined by the assay protocol. Then the magnetic particles MP are transferred into the segment S/R1/R2 and allowed to mix for an additional amount of time. Thereafter, the magnetic particles need to be separated, washed a few times and reacted with a final reagent to cause a detectable response in proportion to the analyte concentration in the sample.

Figure 31A:
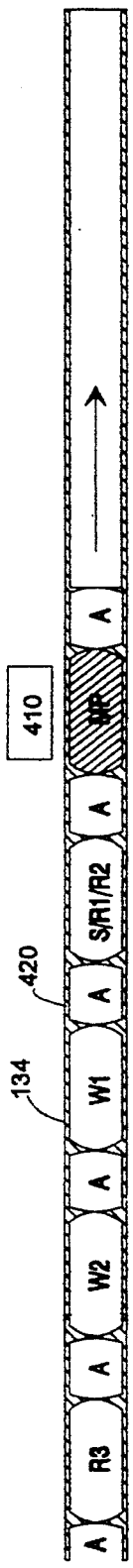
FIGS. 31A—H are schematics of a detail of FIG. 30 showing the steps of one embodiment of a method according to the present invention.
Figure 31B:
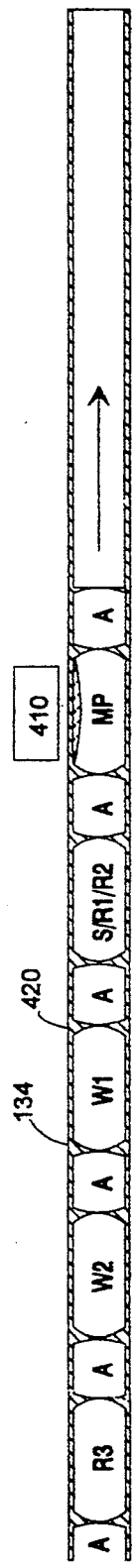

This method is carried out according to the present invention and the sequence of operation of this method is shown in FIGS. 31A–31H. The magnet 410 outside the teflon tube 134 is activated or brought within a close distance to the tube, as the segment with the magnetic particles is situated adjacent thereto as shown in FIG. 31A. At this time, the particles, which were in suspension, are held against the wall of the tube 134 with the film of isolating liquid 420 therebetween as shown in FIG. 31B.

Figure 31C:
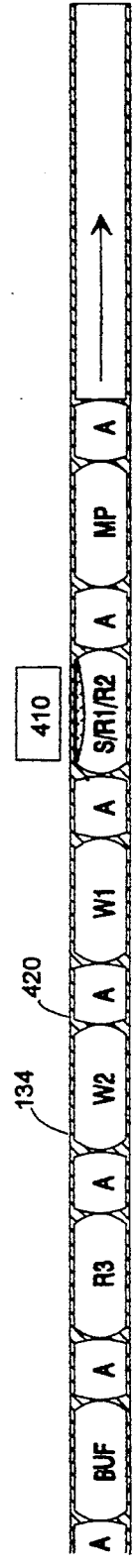
Figure 31D:
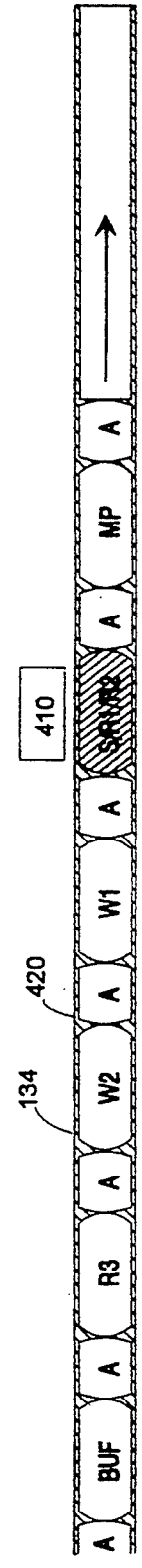

The stream of segments continues to move forward as shown in FIG. 31C whereupon the sample and reagent segment S/R1/R2 has the held down particles therein. At this time, the magnet 410 is deactivated or moved away from the tube and the magnetic particles are allowed to disperse within the S/R1/R2 segment as shown in FIG. 31D.

Figure 31E:
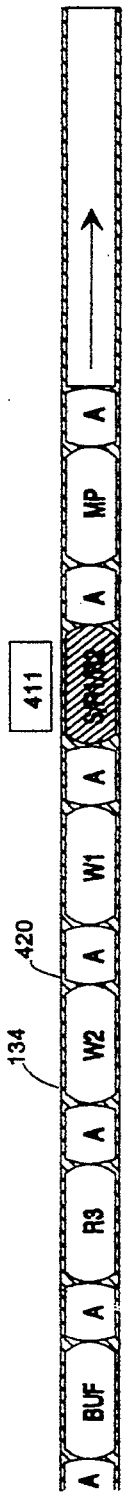

The stream of segments continues to move forward until segment S/R1/R2 with magnetic particles MP arrives at magnet 411 as shown in FIG. 31E. As a result of the deactivation or moving away of the magnet 410 and the flow of the segments, the particles MP become suspended in segment S/R1/R2 as it travels toward magnet 411.

Figure 31F:
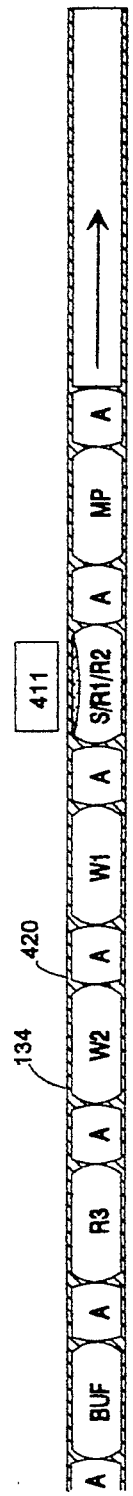

Magnet 411 is then activated or moved toward tube 134 pulling the particles toward the wall thereof as shown in FIG. 31F.

Figure 31G:
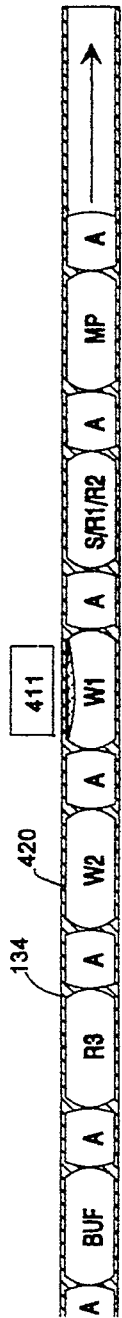
Figure 31H:

The magnetic particles are continued to be held down until the first wash solution W1 arrives at the magnet 411 as shown in FIG. 31G, whereupon the magnet is deactivated or moved away from the teflon tube and the particles are allowed to move into suspension in the wash solution as shown in FIG. 31H.

The internal circulation flow within the wash solution segment and high velocity of the stream provides agitation for washing efficiency. A variable magnetic field may be used at this point to provide additional agitation of the resuspended particles to further improve washing efficiency particularly for the unidirectional flow.

These steps are repeated to wash the magnetic particles as many times as defined by the assay protocol. The steps shown in FIGS. 31E–H can be repeated at magnet 412 for wash W2 or can be repeated at magnet 411 if the direction of flow is reversed and the segment containing the magnetic particles is brought to a position to the left of magnet 411 in FIG. 30. After the last wash, the magnetic particles are released in the final reagent R3 to generate photometric, chemiluminescent and/or fluorescent signals which are measured with detector 144.

As can be seen from the above, the immunoassay method and apparatus does not require any additional hydraulic mechanisms for washing the magnetic particles and conducting a solid phase heterogeneous ligand binding assay. A single probe can be used for aspirating the sample, all reagents including the magnetic particles and the wash solutions. Thus the method and apparatus according to the present invention can be used with the reversible direction system described hereinbefore as well as in prior art unidirectional capsule flow devices.

In accordance with the present invention, a single conduit can be used for the sample, solid phase and other reagents and wash buffer and there is no need for separate conduits, pumps, valves, etc. to wash the magnetic particles.

The washing in accordance with the present invention is more effective than that shown in the prior art, since the magnetic particles are allowed to suspend and agitate in the wash buffer as opposed to merely allowing the wash buffer to flow past the magnetic particle surface. As a result, the total volume of wash solution can be significantly less, e.g., as little as 30 microliters for a single wash.

In one embodiment of the present invention, magnetic particles in the range between $2.5\mu$ and $25\mu$ in diameter were used with an isolating fluid of FC43 fluorocarbon oil. The film of the fluorocarbon oil coating the inner surface of the tube 134 has a thickness of 10 to $50\mu$, preferably $40\mu$. While the diameter of the particles can range from an order of magnitude smaller to an order of magnitude larger than the film thickness, it was found to operate particularly well when the film thickness was of the same order of magnitude as the diameter of the particles and preferably greater than the diameter of the particles in order to prevent the particles from touching the wall.

The magnetic field is applied to a lengthwise limited section of the tube to cause the magnetic particles to accumulate and remain confined in that section. In a preferred embodiment of the present invention, the magnetic field is created by a permanent magnet comprising neodymium-iron-boron high-energy density magnetic material. Variation of the magnetic field can be used to accelerate resuspension. For example, the magnetic field, which normally has a strength of about 2000 gauss, can be varied from strong to weak, can be removed or displaced, or can be spatially varied by placing it on diametrically opposite sides of the tube section.

The embodiment shown in FIG. 30 is particularly advantageous when used in the reverse direction system disclosed with regard to FIGS. 1–29.

The test package or capsule shown in FIG. 30 comprises five segments, magnetic particles MP, a sample plus the first reagent and the second reagent S/R1/R2, the first wash W1, the second wash W2 and the third reagent R3. During every cycle, aspiration of a new segment is done in parallel with a reversible motion of the stream in the analytical line. Thus it takes five cycles to aspirate a full capsule. A liquid buffer segment may be aspirated between capsules, e.g., to improve optical separation among neighboring chemiluminescent capsules. For simplicity the system shown in FIG.

30 is illustrated with only four capsules in the manifold, each representing a different stage in the assay.

The first capsule shown in tube 50 has just been aspirated. The second capsule shown in front of the first magnet 410 is at the stage when the magnetic particles are about to be transferred into the S/R1/R2 segment.

The next capsule shown at the second magnet station 411, is at a stage where the particles will undergo three transfers to W1, W2 and then to R3 in three consecutive cycles.

The last capsule is shown at the optical head of the luminometer 138 when the intensity of luminescence of reagent R3 is measured for about one second. Alternately, the particles can be transferred into the MP segment of the next following capsule which is now devoid of its own particles or into the liquid buffer segment between capsules. After the magnetic particles are removed from it, the R3 segment is pushed through the optical head, where the intensity of its luminescence is measured.

It will be readily apparent to one skilled in the art that between the capsules shown in the schematic there can be one or more other capsules as indicated by the broken lines in FIG. 30. Also, each capsule may contain more or less than five segments as wash segments are added to or removed from the capsule. Moreover, the embodiment shown in FIG. 30 can use a second syringe mechanically linked to pump 100 for better control of the stream motion. The system can also use a syringe linked with pump 31 for extracting waste from the analytical line 134 at the waste manifold 135.

Various other changes may be made in the hereindisclosed best mode embodiment of the sample liquid analysis system and method of our invention without departing from the spirit and scope thereof as defined in the appended claims.

What is claimed is:

1. An analysis apparatus comprising: a fluid conduit; means for forming a plurality of fluid capsules in the conduit for flow therethrough wherein each fluid capsule comprises a plurality of discrete isolated segments including at least one of each of a wash segment, a reagent segment, a sample segment and a segment of suspended magnetic particles, said means comprising means for forming a film of isolating liquid on an inner surface of the conduit and means for randomly aspirating each of a plurality of liquids selected from a sample liquid, reagents, washes and a magnetic particle suspension to form each segment in any order; means for reversibly directing a flow of the fluid capsules in two longitudinal directions of the conduit; magnetic means disposed along the conduit for selectively retaining the suspended magnetic particles from one segment in one capsule in place at a location adjacent to the magnetic means for placement into suspension in another segment in said one capsule during the flow of the one capsule through the conduit; and means disposed along the conduit for measuring the fluid capsules therein.

2. The analysis apparatus according to claim 1, wherein the magnetic means has means for transferring the magnetic particles of one segment of one capsule into at least one other segment of that capsule.

3. The analysis apparatus according to claim 2, wherein the magnetic means has means for varying the magnetic field at the conduit to agitate the suspended particles.

4. The analysis apparatus according to claim 1, wherein the plurality of liquids includes washes for the magnetic particles, wherein the means for randomly aspirating comprises means for forming at least two isolated wash segments in each capsule and wherein the magnetic means comprises means for washing the magnetic particles of one capsule in each of the wash segments of that capsule.

5. The analysis apparatus according to claim 4, wherein the magnetic means has means for transferring the magnetic particles of one segment of one capsule into the wash segments of that capsule.

6. The analysis apparatus according to claim 5, wherein the magnetic means has means for varying the magnetic field at the conduit to agitate the suspended particles.

7. The analysis apparatus according to claim 1, wherein the isolating film has a given thickness and wherein the magnetic particles have a diameter which is on the order of the given thickness.

8. The analysis apparatus according to claim 1, wherein the means for reversibly directing the flow of the fluid capsules comprises means for reversing the flow of the fluid capsules in the conduit from one longitudinal direction to a reverse longitudinal direction.

9. The analysis apparatus according to claim 8, wherein the magnetic means has means for transferring the magnetic particles of one segment of one capsule into at least one other segment of that capsule during the reversible flow of the capsule.

10. The analysis apparatus according to claim 9, wherein the magnetic means has means for varying the magnetic field at the conduit to agitate the suspended particles.

11. The analysis apparatus according to claim 8, wherein the plurality of liquids include washes for the magnetic particles, wherein the means for randomly aspirating comprises means for producing at least two isolated wash segments in each capsule and wherein the magnetic means comprises means for washing the magnetic particles of one capsule in each of the wash segments of that capsule during the flow of the capsule in said reverse longitudinal direction.

12. The analysis apparatus according to claim 11, wherein the magnetic means has means for transferring the magnetic particles of one segment of one capsule into the wash segments of that capsule during the flow in said reverse longitudinal direction.

13. The analysis apparatus according to claim 12, wherein the magnetic means has means for varying the magnetic field at the conduit to agitate the suspended particles.

14. The analysis apparatus according to claim 8, wherein the isolating film has a given thickness and wherein the magnetic particles have a diameter which is less than the given thickness.

15. An analysis method comprising the steps of: forming a plurality of fluid capsules in a fluid conduit for flow therethrough wherein each fluid capsule comprises a plurality of discrete isolated segments including at least one of each of a wash segment, a reagent segment, a sample segment and a segment of suspended magnetic particles; forming a film of isolating liquid on an inner surface of the conduit and randomly aspirating each of a plurality of liquids selected from a sample liquid, reagents, washes and a magnetic particle suspension to form isolated segments from said plurality of liquids in each each segment in any order; reversibly directing a flow of the liquid capsules in two longitudinal directions of the conduit; selectively magnetically retaining the suspended magnetic particles from one segment in one capsule in place at a given location for placement of the magnetic particles into suspension in another segment in said one capsule during the flow of the one capsule through the conduit; and measuring the fluid capsules in the conduit.

16. The analysis method according to claim 15, wherein the step of reversely directing the flow of the fluid capsules comprises reversing the flow of the capsules in the conduit from one longitudinal direction to a reverse longitudinal direction.

17. The analysis method according to claim 15, wherein the plurality of liquids include at least two washes for the magnetic particles, wherein the step of randomly aspirating comprises producing at least two isolated wash segments in each capsule and wherein the step of magnetically retaining comprises washing the magnetic particles of one capsule in each of the wash segments of that capsule.

18. The analysis method according to claim 15, wherein the step of magnetically retaining comprises transferring the magnetic particles of one segment of one capsule into another segment of that capsule.

19. The analysis method according to claim 18, further comprising the step of varying the magnetic field at the conduit to agitate the suspended particles.

20. The analysis method according to claim 15, wherein the isolating film has a given thickness and wherein the magnetic particles have a diameter which on the order of the given thickness.

21. An analysis method comprising the steps of:
a) forming at least one fluid capsule in a fluid conduit, wherein each fluid capsule comprises a plurality of discrete segments isolated by isolating liquid therearound and including at least one wash segment, at least one reagent segment, at least one sample segment and one segment of suspended magnetic particles;

b) directing a flow of the at least one fluid capsule in a forward longitudinal direction of the fluid conduit to position a segment with suspended magnetic particles at first magnetic means;
c) retaining the magnetic particles at the first magnetic means against a wall of the conduit with the isolating liquid therebetween;
d) moving the at least one capsule in the forward longitudinal direction, while the magnetic particles are retained, to position a sample segment at the first magnetic means;
e) dispersing the retained magnetic particles in the sample segment;
f) moving the at least one capsule in the forward longitudinal direction to position the sample segment at second magnetic means;
g) retaining the magnetic particles at the second magnetic means against the wall of the conduit with the isolating liquid therebetween;
h) moving the at least one capsule in the forward longitudinal direction, while the magnetic particles are retained, to position a wash segment at the second magnetic means;
i) dispersing the retained magnetic particles in the wash segment;
j) moving the at least one capsule in the forward direction and then in a reverse direction to position the wash segment at the second magnetic means;
k) repeating step g)–j) for each subsequent wash segment in the at least one capsule.

22. The method according to claim 21, further comprising varying a magnetic filed at the second magnetic means to agitate the suspended particles in the wash segment.

23. The analysis method according to claim 21, wherein the isolating film has a given thickness and wherein the magnetic particles have a diameter which is on the order of the given thickness.

* * * * *